United States Patent
Sekiya et al.

(10) Patent No.: US 9,915,637 B2
(45) Date of Patent: Mar. 13, 2018

(54) GAS SENSOR

(71) Applicant: NGK INSULATORS, LTD., Nagoya-shi, Aichi (JP)

(72) Inventors: Takayuki Sekiya, Nisshin (JP); Mika Murakami, Nagoya (JP); Shingo Sokawa, Anjo (JP); Yosuke Okabe, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 139 days.

(21) Appl. No.: 14/865,471

(22) Filed: Sep. 25, 2015

(65) Prior Publication Data

US 2016/0011159 A1    Jan. 14, 2016

Related U.S. Application Data

(63) Continuation of application No. PCT/JP2014/058423, filed on Mar. 26, 2014.

(30) Foreign Application Priority Data

Mar. 28, 2013  (JP) .................................. 2013-068868

(51) Int. Cl.
  *G01N 7/00*  (2006.01)
  *G01N 33/00*  (2006.01)
  (Continued)

(52) U.S. Cl.
  CPC ...... *G01N 33/0036* (2013.01); *G01M 15/102* (2013.01); *G01M 15/104* (2013.01); *G01N 27/4077* (2013.01); *G01N 33/0037* (2013.01)

(58) Field of Classification Search
  CPC ..................... G01N 33/0036; G01N 27/4077
  (Continued)

(56) References Cited

U.S. PATENT DOCUMENTS

2008/0156644 A1    7/2008  Suzuki et al.
2011/0126610 A1    6/2011  Sekiya et al.
2011/0283774 A1   11/2011  Sekiya et al.

FOREIGN PATENT DOCUMENTS

EP    2333534 A2    6/2011
EP    2388577 A2   11/2011
(Continued)

OTHER PUBLICATIONS

The Extended European Search Report for the corresponding European application No. 14775386.7 dated Nov. 17, 2016.
(Continued)

*Primary Examiner* — John Fitzgerald
*Assistant Examiner* — Rodney T Frank
(74) *Attorney, Agent, or Firm* — Global IP Counselors, LLP

(57) ABSTRACT

First inner gas holes 134a and first outer gas holes 144a of a gas sensor are formed so that the following conditions are satisfied: a first-inner-hole count Nin≥3, 0<an inner/outer hole count ratio Nr≤0.5, and 0<an inner/outer hole-area ratio Ar≤0.25, where the first-inner-hole count Nin represents the number of first inner gas holes 134a, a first-inner-hole average area Ain [mm²] represents (the total opening area of the first inner gas holes 134a)/(the first-inner-hole count Nin), a first-outer-hole count Nout represents the number of the first outer gas holes 144a, a first-outer-hole average area Aout represents (the total opening area of the first outer gas holes 144a)/(the first-outer-hole count Nout), the inner/outer hole count ratio Nr represents the first-inner-hole count Nin/the first-outer-hole count Nout, and the inner/outer hole-area ratio Ar represents the first-inner-hole average area Ain/the first-outer-hole average area Aout.

10 Claims, 21 Drawing Sheets

(51) Int. Cl.
*G01N 27/407* (2006.01)
*G01M 15/10* (2006.01)
(58) Field of Classification Search
USPC .......................................................... 73/23.31
See application file for complete search history.

(56) References Cited

FOREIGN PATENT DOCUMENTS

| EP | 2594927 A2 | 5/2013 |
|---|---|---|
| JP | 2003-172193 A | 6/2003 |
| JP | 2008-164411 A | 7/2008 |
| JP | 2011-112557 A | 6/2011 |
| JP | 2012-2805 A | 1/2012 |

OTHER PUBLICATIONS

The International Preliminary Report on Patentability for the corresponding International patent application No. PCT/JP2014/058423 dated Oct. 8, 2015.

$\theta hmax = max(\theta h1, \theta h2 \cdots, \theta h6)$ $\theta vmax = max(\theta v1, \theta v2, \cdots, \theta v6)$ $\theta\,\text{outmax} = \max(\theta\,\text{out1}, \theta\,\text{out2}, \cdots, \theta\,\text{out12})$ $\theta\,\text{inmax} = \max(\theta\,\text{in1}, \theta\,\text{in2}, \theta\,\text{in3})$

GAS SENSOR

BACKGROUND OF THE INVENTION

1. Field of the Invention

The present invention relates to a gas sensor.

2. Description of the Related Art

A gas sensor that detects the concentration of predetermined gas, such as NOx or oxygen, in gas to be measured (e.g., exhaust gas of a motor vehicle) has been known. Such a gas sensor may be cracked since, for example, water generated when an engine starts is deposited onto a sensor element and, thus, the temperature of the sensor element drops. To prevent such an issue, a technique to attach a protection cover to cover the sensor element is proposed. For example, PTL 1 describes a gas sensor having a double structure protection cover provided on the outer periphery of the tip end portion of the sensor element and having a vent hole for leading exhaust gas to the inside.

CITATION LIST

Patent Literature

PTL 1: JP 2011-112557 A

SUMMARY OF INVENTION

For such a gas sensor, a demand for rapidly detecting a change in the gas concentration in measured gas, that is, a demand for increasing the responsiveness of a gas concentration detection process has arisen. In addition, a demand for preventing the sensor element from being cooled by the gas flow of the measured gas or deposition of water has arisen in order to prevent a decrease in the sensitivity of detection of the sensor element or an increase in power consumption of a heater that keeps the sensor element warm. If, for example, a flow channel of the measured gas inside the protection cover is simplified in order to increase the responsiveness of a gas concentration detection process, the flow rate of the measured gas around the sensor element increases and, thus, the sensor element is easily cooled. In contrast, if the flow channel inside the protection cover is complicated in order to prevent the sensor element from being cooled, the time required for the measured gas to reach the sensor element increases and, thus, the responsiveness of a gas concentration detection process decreases. Thus, there is a need for a gas sensor that provides both quick responsiveness and excellent heat retaining properties.

To solve such a problem, it is a main object of the present invention to provide a gas sensor that provides quick responsiveness of a gas concentration detection process and an excellent heat retaining properties of the sensor element.

According to the present invention, a gas sensor includes a sensor element capable of detecting the concentration of predetermined gas in measured gas, an inner protection cover having a bottomed cylindrical shape and covering a tip end of the sensor element, where the inner protection cover has at least three first inner gas holes and at least one second inner gas hole formed at a position further away in a tip direction of the sensor element than the first inner gas holes, an outer protection cover having a bottomed cylindrical shape and covering the inner protection cover, where the outer protection cover includes a cylindrical body portion having a plurality of first outer gas holes formed therein and a bottomed cylindrical tip end portion having at least one second outer gas hole formed therein and having an inner diameter that is smaller than an inner diameter of the body portion, a first gas chamber formed as a space between the body portion of the outer protection cover and the inner protection cover, where the first gas chamber communicates with the inside of the inner protection cover through the first inner gas holes, and a second gas chamber formed as a space between the tip end portion of the outer protection cover and the inner protection cover, where the second gas chamber does not directly communicate with the first gas chamber and communicates with the inside of the inner protection cover through the second inner gas hole.

The first inner gas holes and the first outer gas holes are formed so that the following conditions are satisfied: $0<$ an inner/outer hole count ratio $Nr \leq 0.5$ and $0<$ an inner/outer hole-area ratio $Ar \leq 0.25$ (where the first-inner-hole count Nin represents the number of first inner gas holes, a first-inner-hole average area Ain [$mm^2$] represents (the total opening area of the first inner gas holes)/(the first-inner-hole count Nin), a first-outer-hole count Nout represents the number of the first outer gas holes, a first-outer-hole average area Aout [$mm^2$] represents (the total opening area of the first outer gas holes)/(the first-outer-hole count Nout), the inner/outer hole count ratio Nr represents the first-inner-hole count Nin/the first-outer-hole count Nout, and the inner/outer hole-area ratio Ar represents the first-inner-hole average area Ain/the first-outer-hole average area Aout).

The gas sensor according to the present invention allows the measured gas to flow into the first gas chamber located inside the outer protection cover through the first outer gas holes. In addition, the measured gas can reach the sensor element inside the inner protection cover from the first gas chamber through the first inner gas holes. Furthermore, the first inner gas holes and the first outer gas holes are formed so that $0<$the inner/outer hole count ratio $Nr \leq 0.5$ and $0<$the inner/outer hole-area ratio $Ar \leq 0.25$. That is, the number of the first outer gas holes (the first-outer-hole count Nout) is twice the number of the first inner gas holes (the first-inner-hole count Nin) or greater, and the opening area per one first outer gas hole (the first-outer-hole average area Aout) is four times the opening area per one first inner gas hole (the first-inner-hole average area Ain) or larger. In this manner, since the number of the first outer gas holes and the average area of the first outer gas holes are relatively large, the flow rate of the measured gas flowing from the outside of the gas sensor into the first gas chamber is relatively high. In contrast, since the number of the first inner gas holes and the average area of the first inner gas holes are relatively small, the flow rate of the measured gas flowing from the first inner gas holes into the inside of the inner protection cover is relatively low. Thus, a decrease in the flow rate of the measured gas flowing from the first gas chamber to the inside of the inner protection cover is compensated by an increase in the flow rate of the measured gas flowing from the outside into the first gas chamber. Thus, an increase in the total time required for the measured gas flowing from the outside into the inside of the inner protection cover via the first gas chamber can be prevented. That is, a decrease in the responsiveness of the gas concentration detection can be prevented. In addition, since the flow rate of the measured gas flowing to the sensor element (the flow rate of the measured gas flowing from the first gas chamber into the inside of the inner protection cover) is regulated, the sensor element is prevented from cooling. In this manner, the responsiveness of gas concentration detection of the gas sensor and the high heat-retaining effect of the sensor element can be obtained at the same time. As used herein, the term "tip direction of the sensor element" refers to a direction from the rear end to the tip end of the sensor element. Note that in the gas sensor according to the present invention, the number of the first inner gas holes is 3 or more (the first-inner-hole count Nin≥3), and 0<the inner/outer hole count ratio Nr≤0.5. Accordingly, the first-outer-hole count Nout≥6. Alternatively, the first inner gas holes and the first outer gas holes may be formed so that 0<the inner/outer hole count ratio Nr≤0.25. Still alternatively, the first inner gas holes and the first outer gas holes may be formed so that 0.25≤the inner/outer hole count ratio Nr≤0.5.

In the gas sensor according to the present invention, the body portion of the outer protection cover may include a side portion having a side surface extending in the direction of the central axis of the outer protection cover and a stepped portion that connects the side portion to the tip end portion. The plurality of first outer gas holes may include at least three horizontal holes formed in the side portion of the outer protection cover and at least three vertical holes formed in the stepped portion of the outer protection cover. In addition, the horizontal holes may be formed so that 0≤a horizontal hole non-existence maximum angle θhmax≤180° (note that when the horizontal holes and the central axis of the outer protection cover are projected onto a plane that is perpendicular to the central axis and the plane is viewed from the central axis in a radial direction of the outer protection cover, an area of the plane in which a projected horizontal hole does not exist is referred to as a "horizontal hole non-existence area". In addition, the largest angle among the central angles of the horizontal hole non-existence areas is referred to as a "horizontal hole non-existence maximum angle θhmax"). The vertical holes may be formed so that 0≤the vertical hole non-existence maximum angle θvmax≤180° (note that when the vertical hole and the central axis of the outer protection cover are projected onto a plane that is perpendicular to the central axis and the plane is viewed from the projected central point in a radial direction of the outer protection cover, an area of the plane in which a projected vertical hole does not exist is referred to as a "vertical hole non-existence area". In addition, the largest angle among the central angles of the vertical hole non-existence areas is referred to as a "vertical hole non-existence maximum angle θvmax"). When the measured gas flows in a direction perpendicular to the central axis of the outer protection cover, the measured gas strikes the tip end portion of the outer protection cover in the upstream of the measured gas and, thus, a flow of the measured gas in the direction of the central axis is generated. Accordingly, the measured gas easily enters the vertical holes. In addition, a gas flow that flows around the outer peripheral surface of the outer protection cover is generated in the downstream of the measured gas, the measured gas easily enters the horizontal holes. Accordingly, since the first outer gas holes include the horizontal holes and the vertical holes, the flow rate of the measured gas from the outside into the first gas chamber can be increased, and the responsiveness of gas concentration detection can be increased. In addition, the holes are formed so that the following conditions are satisfied: the number of the horizontal holes is three or greater, the number of the vertical holes is three or greater, 0≤the horizontal hole non-existence maximum angle θhmax≤180°, and 0≤the vertical hole non-existence maximum angle θvmax≤180°, the vertical holes can be easily formed in the upstream of the measured gas and the horizontal holes can be easily formed in the downstream of the measured gas even when the measured gas flows in any direction of the outer peripheral surface of the outer protection cover. That is, a change in the flow rate of the measured gas flowing from the outside into the first gas chamber caused by the effect of the positional relationship between the direction in which the measured gas flows in the outside and the direction of the outer protection cover can be prevented. In this manner, the effect that improves the responsiveness of gas concentration detection can be more reliably obtained. In this case, to more reliably obtain the effect that improves the responsiveness of gas concentration detection, it is desirable that the conditions the horizontal hole non-existence maximum angle θhmax≤120° and the vertical hole non-existence maximum angle θvmax≤120° be satisfied. In addition, it is more desirable that the condition the horizontal hole non-existence maximum angle θhmax≤(360°/the number of the horizontal holes) be satisfied. Similarly, it is more desirable that the condition the vertical hole non-existence maximum angle θvmax≤(360°/the number of the vertical holes) be satisfied. Furthermore, it is desirable that when the horizontal hole are projected onto a plane that is perpendicular to the central axis of the outer protection cover, the horizontal holes be disposed at equal intervals in the circumferential direction of the outer protection cover. Similarly, it is desirable that when the vertical holes are projected onto a plane that is perpendicular to the central axis of the outer protection cover, the vertical holes be disposed at equal intervals in the circumferential direction of the outer protection cover.

In the gas sensor having the above-described horizontal holes and vertical holes according to the present invention, the horizontal holes and the vertical holes may be formed so as to be alternately disposed in the circumferential direction of the outer protection cover when the horizontal holes and the vertical holes are projected onto a plane that is perpendicular to the central axis of the outer protection cover. In this manner, a change in the flow rate of the measured gas flowing from the outside into the first gas chamber caused by the effect of the positional relationship between the direction in which the measured gas flows in the outside and the direction of the outer protection cover can be more effectively prevented. In this case, it is desirable that when the horizontal holes and the vertical holes are projected onto the plane that is perpendicular to the central axis of the outer protection cover, the distance between the horizontal hole and the neighboring vertical hole in the circumferential direction (the central angle formed by a line from the central axis to an end of the horizontal hole and a line from the central axis to an end of the vertical hole) be the same for all the horizontal holes and vertical holes. This configuration further prevents a change in the flow rate of the measured gas from the outside into the first gas chamber caused by the effect of a positional relationship between the direction in which the measured gas flows in the outside and the direction of the outer protection cover.

In the gas sensor according to the present invention, the first inner gas holes may be formed so that the conditions the first-inner-hole count Nin≥3 and 0≤the first-inner-hole non-existence maximum angle θinmax≤180° are satisfied (note that when the first inner gas holes and the central axis of the inner protection cover are projected onto a plane that is perpendicular to the central axis and the plane is viewed from the projected central point in a radial direction of the inner protection cover, an area of the plane in which a projected first inner gas hole does not exist is referred to as a "first-inner-hole non-existence area". In addition, the largest angle among the central angles of the first-inner-hole non-existence areas is referred to as a "first-inner-hole non-existence maximum angle θinmax"). The first outer gas holes may be formed so that the conditions the first-outerhole count Nout≥6 and 0≤the first-outer-hole non-existence maximum angle θoutmax≤90° are satisfied (note that when the first outer gas holes and the central axis of the outer protection cover are projected onto a plane that is perpendicular to the central axis and the plane is viewed from the projected central point in a radial direction of the outer protection cover, an area of the plane in which a projected first outer gas hole does not exist is referred to as a "first-outer-hole non-existence area". In addition, the largest angle among the central angles of the first-outer-hole non-existence areas is referred to as a "first-outer-hole non-existence maximum angle θoutmax"). In this manner, a change in the flow rate of the measured gas flowing from the outside into the first gas chamber and a change in the flow rate of the measured gas flowing from the first gas chamber into the inside of the inner protection cover caused by the effect of the positional relationship between the direction in which the measured gas flows in the outside and each of the direction of the outer protection cover and the direction of the inner protection cover can be prevented. Thus, the responsiveness of gas concentration detection of the gas sensor and the high heat-retaining effect of the sensor element can be more reliably obtained at the same time. In this case, the first inner gas holes may be formed so that the first-inner-hole count Nin≥3 and 0≤the first-inner-hole non-existence maximum angle θinmax≤120°. In addition, the first outer gas holes may be formed so that the first-outer-hole count Nout≥6 and 0≤the first-outer-hole non-existence maximum angle θoutmax≤60°. In this manner, a change in the flow rate of the measured gas flowing from the outside into the first gas chamber and a change in the flow rate of the measured gas flowing from the first gas chamber into the inside of the inner protection cover caused by the effect of the positional relationship between the direction in which the measured gas flows in the outside and each of the direction of the outer protection cover and the direction of the inner protection cover can be more effectively prevented. Note that it is desirable that the condition the first-inner-hole non-existence maximum angle θinmax≤(360°/the first-inner-hole count Nin) be satisfied. Similarly, it is desirable that the condition the first-outer-hole non-existence maximum angle θoutmax≤(360°/the first-outer-hole count Nout) be satisfied.

In the gas sensor according to the present invention, the first outer gas holes may be formed so that the opening area of each of the first outer gas holes is in the range from 0.196 mm² to 3.14 mm². By setting the opening area of each of the first outer gas holes to 3.14 mm² or less, an unwanted component in the measured gas, such as a water droplet or soot, entering the inside of the outer protection cover through the first outer gas holes can be more effectively prevented. In addition, by setting the opening area of each of the first outer gas holes to 0.196 mm² or greater and, more preferably, 0.785 mm², the measured gas can more reliably flow from the first outer gas holes into the first gas chamber.

In the gas sensor according to the present invention, each of the first inner gas holes may have an opening area of 0.2 mm² or greater. In this manner, clogging of the first inner gas holes due to an unwanted component, such as a soot, in the measured gas can be more effectively prevented.

In the gas sensor according to the present invention, the central point of the opening of each of the first inner gas holes may be located 5 mm or more away from the tip end of the sensor element towards the rear end of the sensor element. The measured gas that has entered the inside of the inner protection cover through the first inner gas holes flows out through the second inner gas holes formed at a point further away in the tip direction of the sensor element than the first inner gas holes. Accordingly, it is difficult for the measured gas to reach the space closer to the rear end of the sensor element than the first inner gas hole. Thus, the time required until the space inside of the inner protection cover is replaced with the measured gas may increase, and the responsiveness of gas concentration detection may decrease. By placing the central point of the opening of the first inner gas hole 5 mm or more away from the tip end of the sensor element towards the rear end of the sensor element, the measured gas is allowed to easily reach the space on the rear side of the sensor element and, thus, a decrease in the responsiveness of gas concentration detection can be more effectively prevented.

In the gas sensor according to the present invention, the second outer gas holes may include at least three horizontal holes formed in the side surface of the tip end portion and at least three vertical holes formed in the bottom surface of the tip end portion.

DESCRIPTION OF THE PREFERRED EMBODIMENTS

Figure 1A:
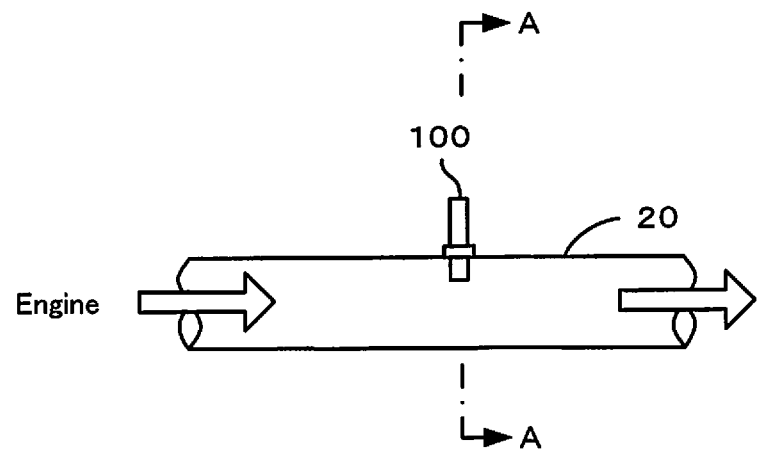
FIG. 1A and FIG. B are schematic illustrations of a gas sensor 100 attached to a pipe 20.
Figure 1B:
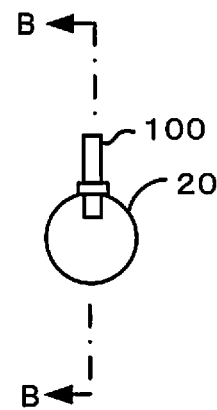
Figure 2:
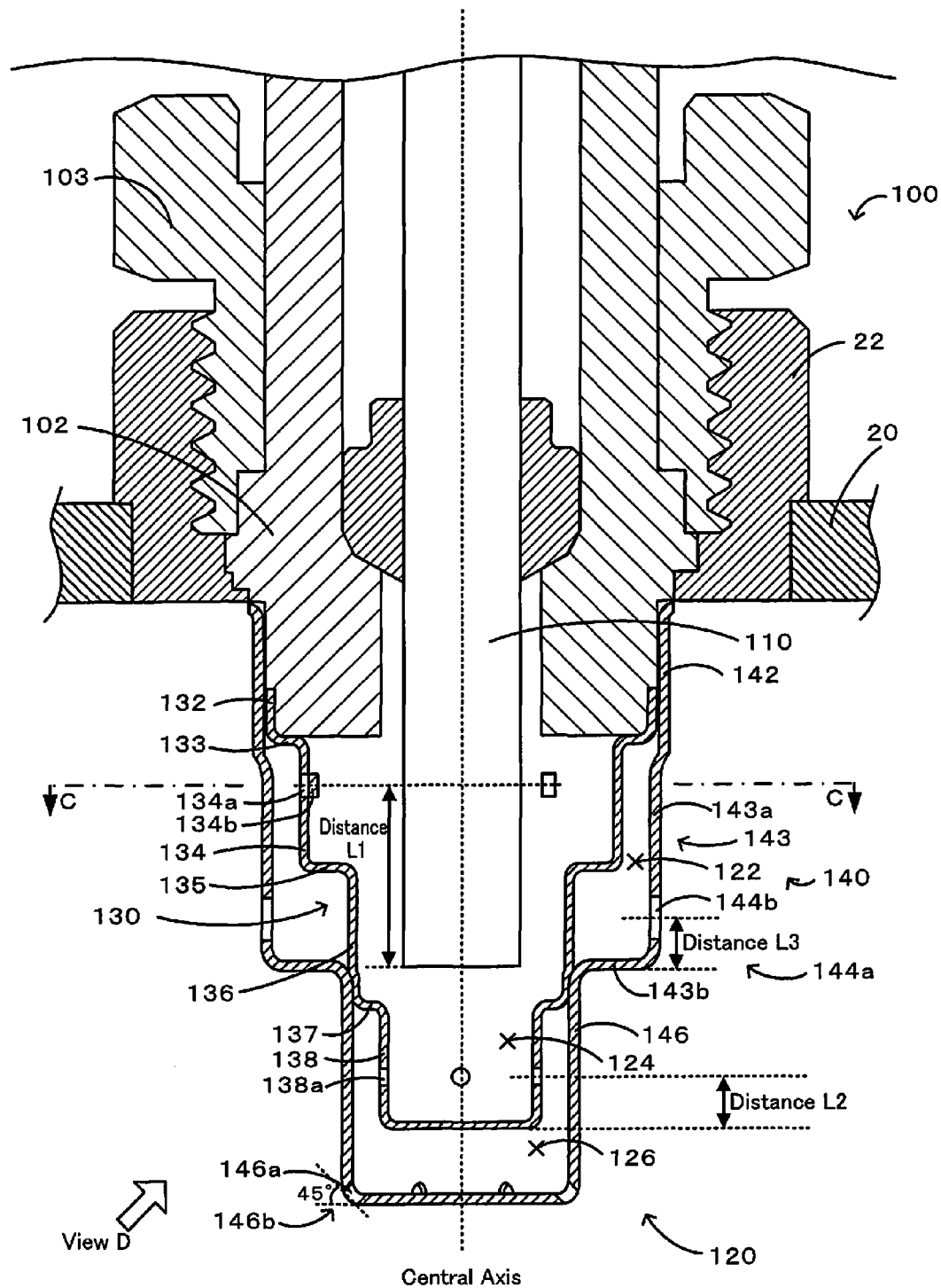
FIG. 2 is a cross-sectional view taken along a line B-B of FIG. 1B
Figure 3:
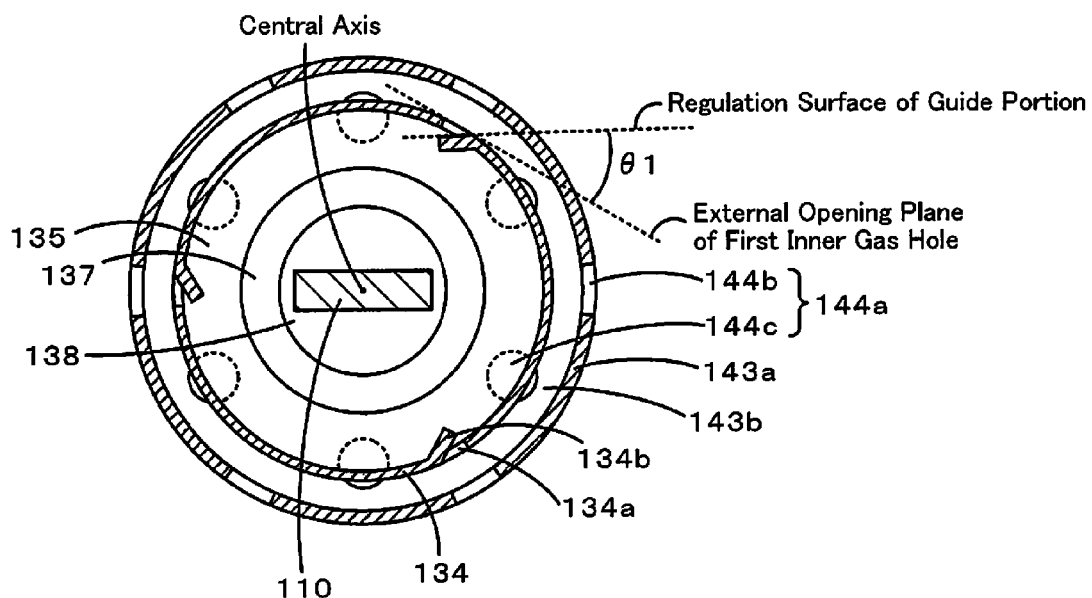
FIG. 3 is a cross-sectional view taken along a line C-C of FIG. 2.
Figure 4:
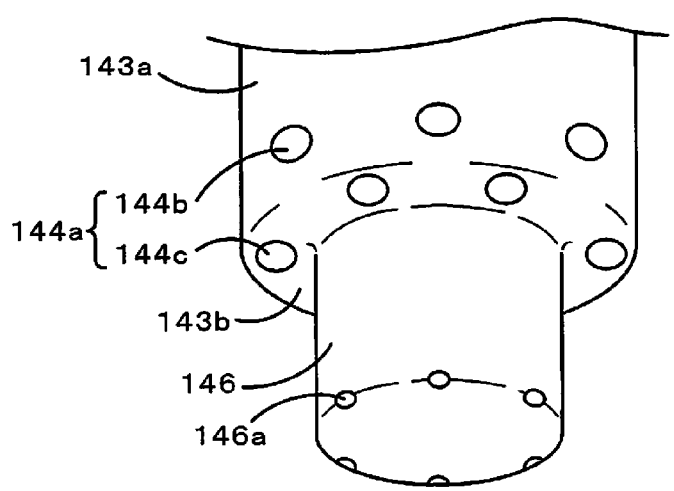
FIG. 4 is a view on Arrow D of FIG. 2.

Embodiments of the present invention are described below with reference to the accompanying drawings. FIG. 1A and FIG. B are schematic illustrations of a gas sensor 100 attached to a pipe 20. FIG. 1A is a view viewed from the side surface of the pipe 20, and FIG. 1B is a cross-sectional view taken along a line A-A of FIG. 1A. FIG. 2 is a cross-sectional view taken along a line B-B of FIG. 1B. FIG. 3 is a cross-sectional view taken along a line C-C of FIG. 2. FIG. 4 is a view on Arrow D of FIG. 2. For convenience of description, in FIG. 2, part of the cross-sectional view taken along a line B-B of FIG. 1B is enlarged.

As illustrated in FIG. 1A, the gas sensor 100 is attached to the inside of the pipe 20, which is an exhaust channel from the engine of a vehicle. The gas sensor 100 detects the concentration of at least one of gas components, such as NOx or $O_2$, contained in exhaust gas output from the engine and serving as measured gas. As illustrated in FIG. 1B, the gas sensor 100 is fixed to the inside of the pipe 20 so that the central axis of the gas sensor 100 is perpendicular to the flow of the measured gas in the pipe 20. Note that the gas sensor 100 may be fixed to the inside of the pipe 20 so that the central axis of the gas sensor 100 is perpendicular to the flow of the measured gas in the pipe 20 and is inclined at a predetermined angle (e.g., 45°) from the vertical.

As illustrated in FIG. 2, the gas sensor 100 includes a sensor element 110 having a function of detecting the concentration of a gas component of the measured gas and a protection cover 120 that protects the sensor element 110. In addition, the gas sensor 100 includes a metal housing 102 and a metal nut 103 having a male screw formed on the outer peripheral surface thereof. The housing 102 is inserted and disposed inside a fixing member 22 welded to the pipe 20 and having a female screw formed on the inner peripheral surface thereof. By further inserting the nut 103 into the fixing member 22, the housing 102 is fixed to the inside of the fixing member 22. In this manner, the gas sensor 100 is fixed to the inside of the pipe 20.

The sensor element 110 is a long and thin plate-like element. The sensor element 110 is formed from an oxygen ion conductive solid electrolyte layer, such as zirconia ($ZrO_2$). The sensor element 110 has a heater thereinside. The heater heats the sensor element 110 and keeps the sensor element 110 warm, that is, the heater performs temperature control of the sensor element 110. Such a structure and a principal of detecting the concentration of a gas component are well-known and is described in, for example, Japanese Unexamined Patent Application Publication No. 2008-164411.

The protection cover 120 is disposed so as to surround the sensor element 110. The protection cover 120 includes a bottomed cylindrical inner protection cover 130 that covers the tip end of the sensor element 110 and a bottomed cylindrical outer protection cover 140 that covers the inner protection cover 130. In addition, a space surrounded by the inner protection cover 130 and the outer protection cover 140 is formed so as to serve as a first gas chamber 122 and a second gas chamber 126. Furthermore, a space surrounded by the inner protection cover 130 is formed so as to serve as a sensor element chamber 124. Note that the gas sensor 100, the inner protection cover 130, and the outer protection cover 140 have the same central axis (i.e., are coaxial).

The inner protection cover 130 is a member made of a metal (e.g., stainless steel). The inner protection cover 130 includes a cylindrical large-diameter portion 132, a cylindrical first body portion 134 having a diameter smaller than that of the large-diameter portion 132, a cylindrical second body portion 136 having a diameter smaller than that of the first body portion 134, and a bottomed cylindrical tip end portion 138 having a diameter smaller than that of the second body portion 136. In addition, the inner protection cover 130 includes a stepped portion 133 that connects the large-diameter portion 132 to the first body portion 134, a stepped portion 135 that connects the first body portion 134 to the second body portion 136, and a stepped portion 137 that connects the second body portion 136 to the tip end portion 138. Note that the large-diameter portion 132, the first body portion 134, the second body portion 136, and the tip end portion 138 have the same central axis. The inner peripheral surface of the large-diameter portion 132 is in contact with the housing 102. Thus, the inner protection cover 130 is fixed to the housing 102. The first body portion 134 and the second body portion 136 are disposed so as to cover the side surface of the sensor element 110. The first body portion 134 has three first inner gas holes 134a and three plate-like guide portions 134b formed therein (refer to FIG. 3). The three first inner gas holes 134a are formed at equal intervals, and the three guide portions 134b are formed at equal intervals. Each of the first inner gas holes 134a allows the first gas chamber 122 and the sensor element chamber 124 to communicate with each other. Each of the guide portions 134b regulates the flow of the measured gas entering the sensor element chamber 124 through one of the first inner gas holes 134a. The side surface of the tip end portion 138 has four second inner gas holes 138a formed therein at equal intervals. Each of the second inner gas holes 138a allows the sensor element chamber 124 and the second gas chamber 126 to communicate with each other.

As illustrated in FIG. 3, the first inner gas holes 134a have a one-to-one correspondence to the guide portions 134b. Each of the guide portions 134b is formed so as to be located between the corresponding one of the first inner gas holes 134a and the sensor element 110. In addition, the guide portions 134b are formed so as to be rotationally symmetrical (threefold symmetrical). Each of the three first inner gas holes 134a is formed so as to have a rectangular opening with an opening area of 0.2 mm$^2$ or greater. By setting the opening area to 0.2 mm$^2$ or greater, clogging of the first inner gas holes 134a caused by an unwanted component such as soot in the measured gas can be more effectively prevented. Note that the opening area of the first inner gas hole 134a is defined as the opening area of the first inner gas holes 134a as viewed in the normal direction of the inner protection cover 130 (the first body portion 134). That is, the opening area of the first inner gas hole 134a is defined as the area of an external opening plane of the first inner gas hole 134a (the opening plane of the outer periphery side of the first body portion 134) as viewed in the direction perpendicular to the external opening plane. In addition, an angle θ1 formed by a regulation surface of the guide portion 134b and the external opening plane of the first inner gas hole 134a (refer to FIG. 3) can be set to an angle greater than or equal to 20° and less than or equal to 70° or an angle greater than or equal to 25° and less than or equal to 67.5°. The first inner gas hole 134a is formed so that the central point of the opening (the central point in the vertical direction of FIG. 2) is located 5 mm or more away from the tip end of the sensor element 110 towards the rear end of the sensor element 110. That is, a distance L1 from the tip end of the sensor element 110 to the central point of the opening of the first inner gas hole 134a (refer to FIG. 2) is 5 mm or greater. Note that according to the present embodiment, the distances L1 for all the three first inner gas holes 134a are the same. If the distances L1 for the first inner gas holes 134a differ from one another, it is desirable that each of the distances L1 be 5 mm or greater.

Each of the second inner gas holes 138a is formed so that the cross-section shape perpendicular to the central axis of the second inner gas hole 138a is an exact circle. Four second inner gas holes 138a are formed. A distance L2 between the central point of each of the second inner gas holes 138a (the central point in the vertical direction of FIG. 2) and the bottom surface of the inner protection cover 130 (the outer peripheral surface of the bottom portion of the tip end portion 138) (refer to FIG. 2) is, for example, 1 mm to 3 mm. In addition, according to the present embodiment, the diameter of the second inner gas hole 138a is in the range, for example, from 0.6 to 1.2 mm, but the diameter is not especially limited thereto. The number of the second inner gas holes 138a is not limited to 4. For example, the number may be 3 to 6. Note that the second inner gas holes 138a are not limited to those formed in the side surface of the tip end portion 138. For example, the second inner gas holes 138a may be formed in the bottom surface of the tip end portion 138 or a boundary portion between the side surface and the bottom surface of the tip end portion 138.

The outer protection cover 140 is a member made of a metal (e.g., stainless steel). The outer protection cover 140 includes a cylindrical large-diameter portion 142, a cylindrical body portion 143 connected to the large-diameter portion 142 and having a diameter smaller than that of the large-diameter portion 142, and a bottomed cylindrical tip end portion 146 having an inner diameter smaller than that of the cylindrical body portion 143. In addition, the body portion 143 includes a side portion 143a that has a side surface extending in the direction of the central axis of the outer protection cover 140 (the vertical direction in FIG. 2), a stepped portion 143b that is a bottom portion of the body portion 143 and that connects the side portion 143a to the tip end portion 146. Note that each of the central axes of the large-diameter portion 142, the body portion 143, the tip end portion 146 is the same as the central axis of the inner protection cover 130. The inner peripheral surface of the large-diameter portion 142 is in contact with the housing 102 and the large-diameter portion 132. Thus, the outer protection cover 140 is fixed to the housing 102. The body portion 143 is disposed so as to cover the outer peripheral surfaces of the first body portion 134 and the second body portion 136. The tip end portion 146 is disposed so as to cover the tip end portion 138, and the inner peripheral surface of the tip end portion 146 is in contact with the outer peripheral surface of the second body portion 136. The outer protection cover 140 includes 12 first outer gas holes 144a formed in the body portion 143 and six second outer gas holes 146a formed in the tip end portion 146.

The first outer gas holes 144a allow the outside of the outer protection cover 140 to communicate with the first gas chamber 122. The first outer gas holes 144a include six horizontal holes 144b formed in the side portion 143a and six vertical holes 144c formed in the stepped portion 143b. A distance L3 between the central point of the horizontal hole 144b (the central point in the vertical direction in FIG. 2) and the outer surface of the stepped portion 143b (the lower surface in FIG. 2) is, for example, 1 mm to 3 mm (refer to FIG. 2), but the distance L3 is not limited thereto. According to the present embodiment, the six horizontal holes 144b are formed so as to have the same distance L3. However, the distances L3 may differ from one another. Each of the first outer gas holes 144a (the horizontal holes 144b and the vertical holes 144c) is drilled so as to have a shape of a circle (an exact circle). By setting the opening area of each of the 12 first outer gas holes 144a formed so as to have an opening area of 0.196 mm$^2$ to 3.14 mm$^2$ to 3.14 mm$^2$ or less, an unwanted component in the measured gas, such as a water droplet or soot, entering the inside of the outer protection cover 140 through the first outer gas holes 144a can be more effectively prevented. In addition, by setting the opening area of each of the first outer gas holes to 0.196 mm$^2$ or more and, more preferably, 0.785 mm$^2$ or more, the measured gas is allowed to reliably flow into the first gas chamber 122 through the first outer gas holes 144a. According to the present embodiment, the opening areas of the 12 first outer gas holes 144a are set to the same value. Note the opening area of the first outer gas hole 144a is defined as the area of the external opening plane of the first outer gas hole 144a as viewed in a direction perpendicular to the external opening plane.

Figure 5:
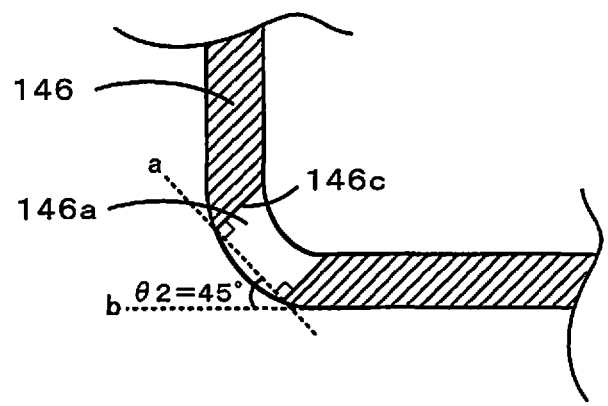
FIG. 5 is an enlarged partial cross-sectional view of the second outer gas hole 146a and its vicinity of FIG. 2.
Figure 6:
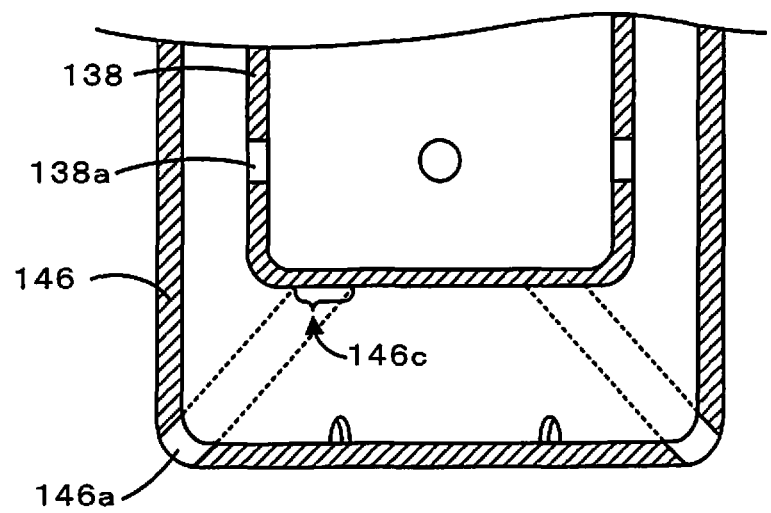
FIG. 6 is an enlarged partial cross-sectional view of the second outer gas hole 146a and the second inner gas hole 138a and their vicinity of FIG. 2.

The second outer gas holes 146a allow the outside of the outer protection cover 140 to communicate with the second gas chamber 126. The second outer gas holes 146a are formed in a corner portion 146b, which is a boundary portion between the side surface and the bottom surface of the tip end portion 146. Six second outer gas holes 146a are formed at equal intervals (refer to FIG. 2 and FIG. 4). Each of the second outer gas holes 146a is a hole drilled so as to have a shape of a circle. FIG. 5 is an enlarged partial cross-sectional view of the second outer gas hole 146a and its vicinity of FIG. 2. FIG. 6 is an enlarged partial cross-sectional view of the second outer gas hole 146a and the second inner gas hole 138a and their vicinity of FIG. 2. As illustrated in FIG. 5, the second outer gas hole 146a is formed so that an angle θ2 formed by the external opening plane of the second outer gas hole 146a and the bottom surface of the tip end portion 146 is in the range from 10° to 80° (45° according to the present embodiment) and an angle formed by the inner peripheral surface of the second outer gas hole 146a and the external opening plane is 90°. In this manner, water entering the onside of the outer protection cover 140 and depositing on the sensor element 110 can be more effectively prevented. In addition, the dependency of the responsiveness of the sensor element 110 on the flow velocity can be reduced. In addition, as illustrated in FIG. 6, a positional relationship between the second outer gas hole 146a and the second inner gas hole 138a is determined so that the second inner gas hole 138a is located at a position other than an area 146c that is located on an extension of the second outer gas hole 146a. As illustrated in the drawing, if imaginary light having a directivity is emitted in a direction along the central axis of the second outer gas holes 146a (a direction that forms 45° with respect to the central axis direction of the outer protection cover 140), the area 146c which the light strikes appears in the bottom surface of the tip end portion 138 of the inner protection cover 130. The area 146c is referred to as an area on an extension of the second outer gas hole 146a. The second inner gas hole 138a is located at a position other than the area 146c. Note that each of the areas of the openings of the six second outer gas holes 146a is the same. The second outer gas hole 146a is formed so that the cross-section shape perpendicular to the central axis thereof is an exact circle. In addition, according to the present embodiment, the diameter of the second outer gas hole 146a is in the range from 0.8 to 1.2 mm. However, the value of the diameter is not limited thereto. Note that the second outer gas holes 146a may be located in an area other than the corner portion 146b, such as the side surface or the bottom surface of the tip end portion 146.

The first gas chamber 122 is a space surrounded by the stepped portions 133 and 135, the first body portion 134, the second body portion 136, the large-diameter portion 142, the side portion 143a, and the stepped portion 143b. The sensor element chamber 124 is a space surrounded by the inner protection cover 130. The second gas chamber 126 is a space surrounded by the stepped portion 137, and the tip end portions 138 and 146. Note that since the inner peripheral surface of the tip end portion 146 is in contact with the outer peripheral surface of the second body portion 136, the first gas chamber 122 does not directly communicate with the second gas chamber 126.

The first outer gas holes 144a and the first inner gas holes 134a are described in detail below. According to the present embodiment, the first inner gas holes 134a and the first outer gas holes 144a are formed so that a first-inner-hole count Nin≥3, 0<an inner/outer hole-count ratio Nr≤0.5, and 0<an inner/outer hole-area ratio Ar≤0.25, where the first-inner-hole count Nin represents the number of the first inner gas holes 134a. A first-inner-hole average area Ain [mm$^2$] represents (the total opening area of the first inner gas holes 134a)/(the first-inner-hole count Nin). A first-outer-hole count Nout represents the number of the first outer gas holes 144a. A first-outer-hole average area Aout [mm$^2$] represents (the total opening area of the first outer gas holes 144a)/(the first-outer-hole count Nout). The inner/outer hole count ratio Nr represents the first-inner-hole count Nin/the first-outer-hole count Nout, and the inner/outer hole-area ratio Ar represents the first-inner-hole average area Ain/the first-outer-hole average area Aout. That is, the number of the first outer gas holes 144a (the first-outer-hole count Nout) is twice the number of the first inner gas holes 134a (the first-inner-hole count Min) or greater, and the opening area per one first outer gas hole 144a (the first-outer-hole average area Aout) is four times the opening area per one first inner gas hole 134a (the first-inner-hole average area Ain) or larger. Note that according to the present embodiment, since the first-inner-hole count Nin=3 and the first-outer-hole count Nout=12, the inner/outer hole count ratio Nr=0.25. Thus, the conditions the first-inner-hole count Nin≥3 and 0<an inner/outer hole-count ratio Nr≤0.5 are satisfied. Note that the holes may be formed so that the condition 0<the inner/outer hole count ratio Nr≤0.25 or the condition 0.25≤the inner/outer hole count ratio Nr≤0.5 is satisfied.

Figure 7:
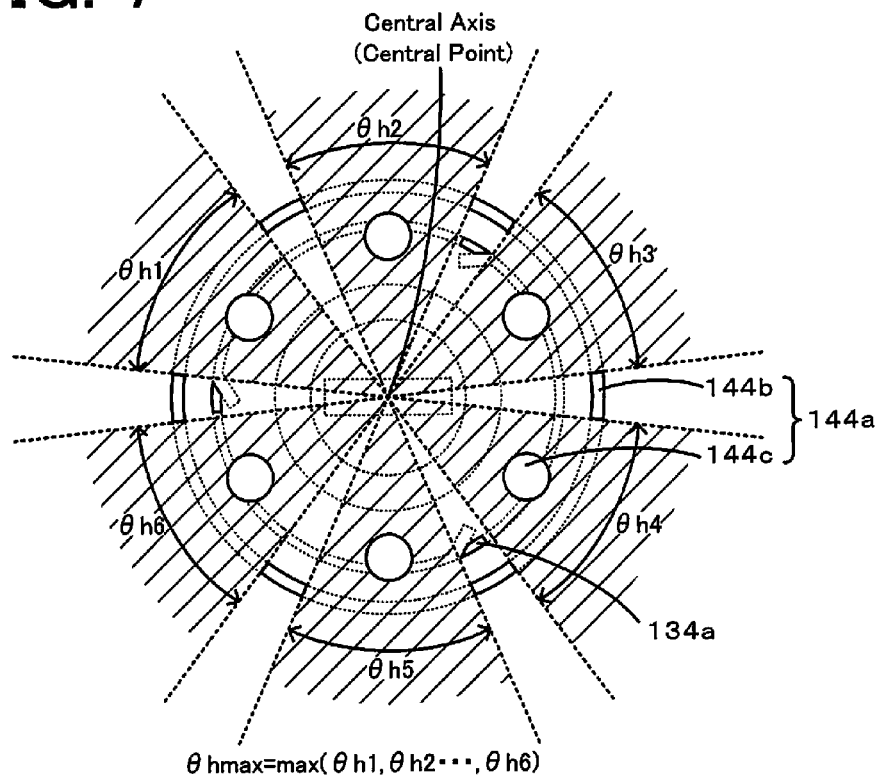
FIG. 7 illustrates the horizontal hole non-existence maximum angle θhmax.
Figure 8:
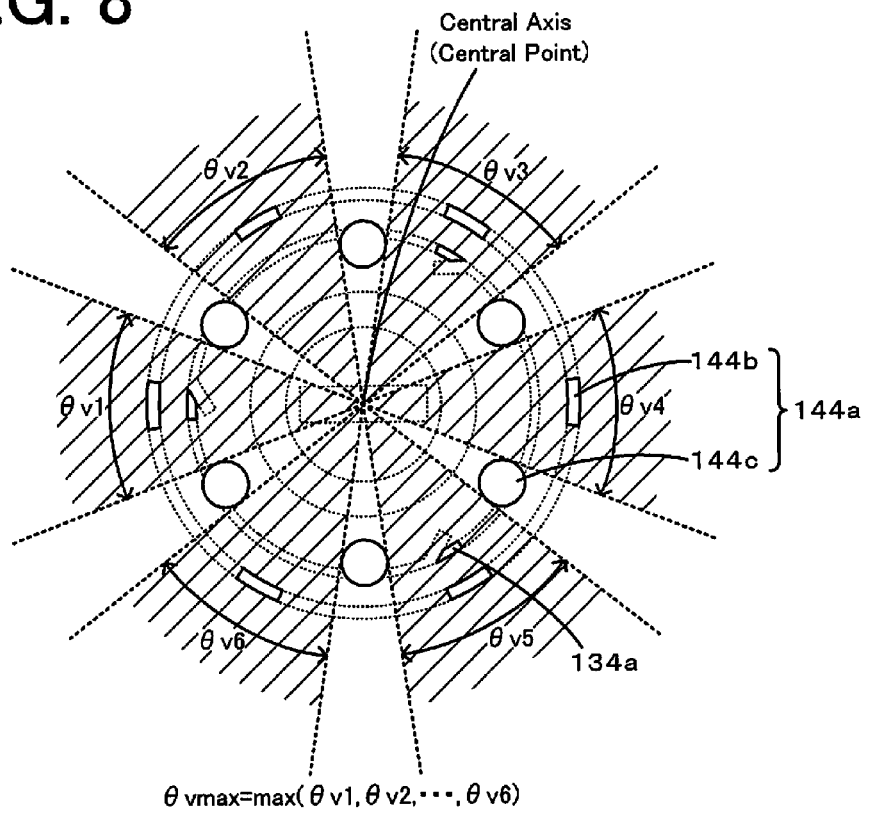
FIG. 8 illustrates the vertical hole non-existence maximum angle θvmax.

In addition, according to the present embodiment, the horizontal holes 144b and the vertical holes 144c are formed so that the number of the horizontal holes 144b is three or more, and the number of the vertical holes 144c is three or more. The horizontal holes 144b are formed so that the condition 0≤a horizontal hole non-existence maximum angle θhmax≤180° is satisfied, and the vertical holes 144c are formed so that 0≤a vertical hole non-existence maximum angle θvmax≤180° is satisfied. In addition, the horizontal holes 144b and the vertical holes 144c are formed so that a condition the horizontal hole non-existence maximum angle θhmax≤120° and a condition the vertical hole non-existence maximum angle θvmax≤120° are also satisfied. As described above, according to the present embodiment, six horizontal holes 144b and six vertical holes 144c are formed. The horizontal hole non-existence maximum angle θhmax and the vertical hole non-existence maximum angle θvmax are described below. FIG. 7 illustrates the horizontal hole non-existence maximum angle θhmax. FIG. 8 illustrates the vertical hole non-existence maximum angle θvmax. In FIGS. 7 and 8, the horizontal holes 144b, the vertical holes 144c, the first inner gas holes 134a, and the central axis of the outer protection cover 140 are projected onto a plane perpendicular to the central axis (e.g., a C-C plane of FIG. 2) (are projected parallel to the central axis). In FIGS. 7 and 8, the projected horizontal holes 144b, vertical holes 144c, and first inner gas holes 134a are shown by solid lines.

The horizontal hole non-existence maximum angle θhmax is described below with reference to FIG. 7. Firstly, the central axis of the outer protection cover 140 is projected onto a plane that is perpendicular to the central axis. When viewed from the projected central axis in the plane (hereinafter, central point) in a radial direction of the outer protection cover 140, an area of the plane in which a projected horizontal hole 144b does not exist is referred to as a "horizontal hole non-existence area". In FIG. 7, a horizontal hole non-existence area is shown as an area with hatchings. For example, according to the present embodiment, six horizontal holes 144b are formed, and half lines each extending from the central point and touching an end portion of a horizontal hole 144b (bold dashed lines in the drawing) can be drawn (12 half lines in FIG. 7). In an area sandwiched by two half lines that pass through adjoining ends of two neighboring horizontal holes 144b, another projected horizontal hole 144b does not exist. Accordingly, this area (an area with hatchings in the drawing) is a horizontal hole non-existence area. As illustrated in the drawing, six horizontal hole non-existence areas exist in the arrangement of the horizontal holes 144b according to the present embodiment. Subsequently, the central angles (an angle formed by two half lines that form a horizontal hole non-existence area) of the six horizontal hole non-existence areas are referred to as "horizontal hole non-existence angles θh1 to θh6". The horizontal hole non-existence maximum angle θhmax is the largest value among the horizontal hole non-existence angles θh1 to θh6. Note that according to the present embodiment, six horizontal holes 144b are disposed along the circumferential direction of the outer protection cover 140 at equal intervals. Accordingly, the horizontal hole non-existence angles θh1 to θh6 are the same and are equal to the horizontal hole non-existence maximum angle θhmax. In addition, 0≤the horizontal hole non-existence maximum angle θhmax (=the horizontal hole non-existence angles θh1 to θh6)<60° (=360°/the number of the horizontal holes 144b). A large horizontal hole non-existence maximum angle θhmax indicates that a portion having a large distance between the neighboring horizontal holes 144b in the circumferential direction exists. That is, a large horizontal hole non-existence maximum angle θhmax indicates that a large area in which the horizontal holes 144b are not consecutively disposed as viewed in the circumferential direction of the outer protection cover 140 exists.

The vertical hole non-existence maximum angle θvmax is described next with reference to FIG. 8. The same concept of the horizontal hole non-existence maximum angle θhmax can apply to the vertical hole non-existence maximum angle θvmax. Firstly, in a plane that is perpendicular to the central axis of the outer protection cover 140, when viewed from the central point, an area of the plane in which a projected vertical hole 144c does not exist is defined as a vertical hole non-existence area. In FIG. 8, a vertical hole non-existence area is shown as an area with hatchings. According to the present embodiment, as illustrated in the drawing, six vertical hole non-existence area are formed, and the central angles of the six vertical hole non-existence areas are referred to as "vertical hole non-existence angles θv1 to θv6". The vertical hole non-existence maximum angle θvmax is the largest value among the vertical hole non-existence angles θv1 to θv6. Note that according to the present embodiment, six vertical holes 144c are disposed along the circumferential direction of the outer protection cover 140 at equal intervals. Accordingly, the vertical hole non-existence angles θv1 to θv6 are the same and are equal to the vertical hole non-existence maximum angle θvmax. In addition, 0≤the vertical hole non-existence maximum angle θvmax (=the vertical hole non-existence angles θv1 to θv6)<60° (=360°/the number of the vertical holes 144c). A large vertical hole non-existence maximum angle θvmax indicates that a portion having a large distance between the neighboring vertical holes 144c in the circumferential direction exists. That is, a large vertical hole non-existence maximum angle θvmax indicates that a large area in which the vertical holes 144c are not consecutively disposed as viewed in the circumferential direction of the outer protection cover 140 exists.

Figure 9:
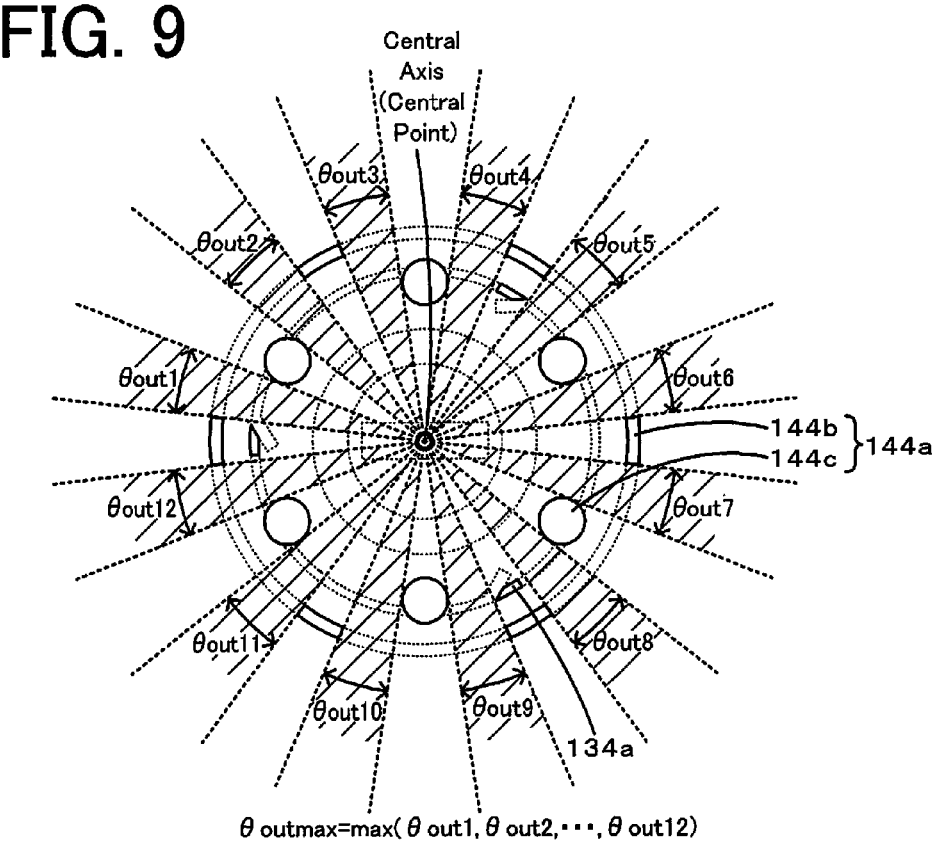
FIG. 9 illustrates the first-outer-hole non-existence maximum angle θoutmax.

In addition, the first outer gas holes 144a are formed so that the first-outer-hole count Nout≥6 and 0≤a first-outer-hole non-existence maximum angle θoutmax≤60°. The first-outer-hole non-existence maximum angle θoutmax is described below. FIG. 9 illustrates the first-outer-hole non-existence maximum angle θoutmax. Like FIG. 7 and FIG. 8, in FIG. 9, the horizontal holes 144b, the vertical holes 144c, the first inner gas holes 134a, and the central axis of the outer protection cover 140 are projected (are projected parallel to the central axis) onto a plane that is perpendicular to the central axis (e.g., a C-C plane in FIG. 2). In FIG. 9, the projected horizontal holes 144b, vertical holes 144c, and first inner gas holes 134a are shown by solid lines. The first-outer-hole non-existence maximum angle θoutmax is described below with reference to FIG. 9. Note that the same concept of the horizontal hole non-existence maximum angle θhmax or the vertical hole non-existence maximum angle θvmax can apply to the first-outer-hole non-existence maximum angle θoutmax. Firstly, in a plane that is perpendicular to the central axis of the outer protection cover 140, when viewed from the central point, ah area of the plane in which projected first outer gas holes 144a (the horizontal holes 144b and the vertical holes 144c) do not exist is defined as a first-outer-hole non-existence area. In FIG. 9, a first-outer-hole non-existence area is shown as an area with hatchings. In the arrangement of the first outer gas holes 144a according to the present embodiment, as illustrated in the drawing, 12 first-outer-hole non-existence areas are formed, and the central angles of the 12 first-outer-hole non-existence areas are defined as first-outer-hole non-existence angles θout1 to θout12. The first-outer-hole non-existence maximum angle θoutmax is the largest value among the first-outer-hole non-existence angles θout1 to θout12. Note that according to the present embodiment, as can be seen from FIG. 9, the horizontal holes 144b and the vertical holes 144c are formed so as to be alternately arranged in the circumferential direction of the outer protection cover 140 as projected to a plane perpendicular to the central axis of the outer protection cover 140. In addition, the horizontal holes 144b and the vertical holes 144c are arranged so that as projected onto a plane perpendicular to the central axis of the outer protection cover 140, the distance between a horizontal hole 144b and a neighboring vertical hole 144c in the circumferential direction (the central angle formed by a line extending from the central axis to an end of the horizontal hole 144b and a line extending from the central axis to an end of the vertical hole 144c) is the same for all the horizontal holes and the vertical holes. Accordingly, the first-outer-hole non-existence angles θout1 to θout12 are the same and are equal to the first-outer-hole non-existence maximum angle θoutmax. In addition, 0≤the first-outer-hole non-existence maximum angle θoutmax (=the first-outer-hole non-existence angles θout1 to θout12)<30° (=360°/the number of the first outer gas holes 144a). A large first-outer-hole non-existence maximum angle θoutmax indicates that a portion having a large distance between the first outer gas holes 144a in the circumferential direction exists. That is, a large first-outer-hole non-existence maximum angle θoutmax indicates that a large area in which the first outer gas holes 144a (the horizontal holes 144b and the vertical holes 144c) are not consecutively disposed as viewed in the circumferential direction of the outer protection cover 140 exists.

Figure 10:
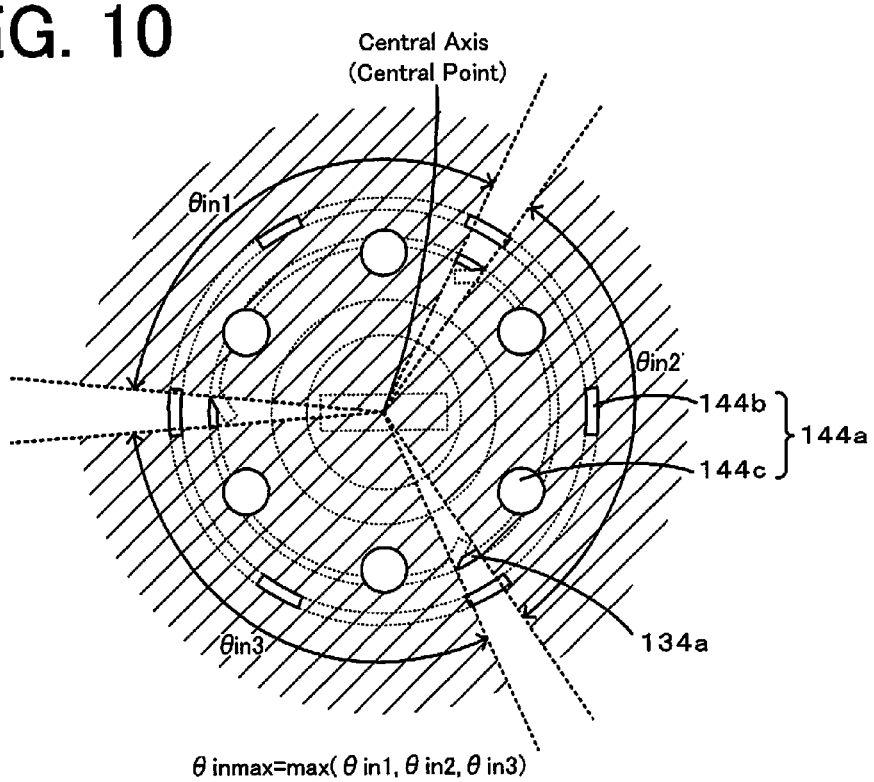
FIG. 10 illustrates the first-inner-hole non-existence maximum angle θinmax.

The first inner gas holes 134a are formed so that the first-inner-hole count Nin≥3 and 0≤a first-inner-hole non-existence maximum angle θinmax≤120°. The first-inner-hole non-existence maximum angle θinmax is described below. FIG. 10 illustrates the first-inner-hole non-existence maximum angle θinmax. In FIG. 10, the horizontal holes 144b, the vertical holes 144c, the first inner gas holes 134a, and the central axis of the inner protection cover 130 are projected onto a plane that is perpendicular to the central axis (e.g., a C-C plane of FIG. 2) (are projected parallel to the central axis). In FIG. 10, the projected horizontal holes 144b, vertical holes 144c, and first inner gas holes 134a are shown by solid lines. The first-inner-hole non-existence maximum angle θinmax is described below with reference to FIG. 10. Note that the same concept of the horizontal hole non-existence maximum angle θhmax, the vertical hole non-existence maximum angle θvmax, or the first-outer-hole non-existence maximum angle θoutmax can apply to the first-inner-hole non-existence maximum angle θinmax. Firstly, in a plane that is perpendicular to the central axis of the inner protection cover 130, when viewed from the central point, an area of the plane in which projected first inner gas holes 134a do not exist is defined as a first-inner-hole non-existence area. In FIG. 10, a first-inner-hole non-existence area is shown as an area with hatchings. In the arrangement of the first inner gas holes 134a according to the present embodiment, as illustrated in the drawing, three first-inner-hole non-existence areas are formed, and the central angles of the three first-inner-hole non-existence areas are defined as first-inner-hole non-existence angles θin1 to θin3. The first-inner-hole non-existence maximum angle θinmax is the largest value among the first-inner-hole non-existence angles θin1 to θin3. Note that according to the present embodiment, since the three first inner gas holes 134a are disposed in the circumferential direction of the inner protection cover 130 at equal intervals, the first-inner-hole non-existence angles θin1 to θin3 are the same and are equal to the first-inner-hole non-existence maximum angle θinmax. In addition, 0≤the first-inner-hole non-existence maximum angle θinmax (=the first-inner-hole non-existence angles θin1 to θin3)<120° (=360°/the first-inner-hole count Nin). A large first-inner-hole non-existence maximum angle θinmax indicates that a portion having a large distance between the neighboring first inner gas holes 134a in the circumferential direction exists. That is, a large first-inner-hole non-existence maximum angle θinmax indicates that a large area in which the first inner gas holes 134a are not consecutively disposed as viewed in the circumferential direction of the outer protection cover 140 exists.

Note that "the horizontal hole non-existence maximum angle θhmax=0°" indicates that the horizontal hole non-existence area does not exist. The same applies to each of the conditions the vertical hole non-existence maximum angle θvmax=0°, the first-outer-hole non-existence maximum angle θoutmax=0°, and the first-inner-hole non-existence maximum angle θinmax=0°.

The flow of the measured gas when the gas sensor 100 having such a configuration detects the concentration of predetermined gas is described below. The measured gas flowing in the pipe 20 enters the first gas chamber 122 through any of the first outer gas holes 144a first. Subsequently, the measured gas enters the sensor element chamber 124 from the first gas chamber 122 through any of the first inner gas holes 134a. Subsequently, the measured gas enters the second gas chamber 126 from the sensor element chamber 124 through any of the second inner gas holes 138a and, thereafter, flows from the second gas chamber 126 to the outside through any of the second outer gas holes 146a. At that time, the power of the internal heater is controlled by a controller (not illustrated) so that the sensor element 110 maintains a predetermined temperature. Then, the sensor element 110 generates an electric signal (a voltage or an electric current) in accordance with the concentration of the predetermined gas (e.g., NOx or $O_2$) in the measured gas located inside the sensor element chamber 124. The gas concentration is detected on the basis of the electric signal.

According to the embodiment described in detail above, the gas sensor 100 allows the measured gas to flow into the first gas chamber 122 located inside the outer protection cover 140 through the first outer gas holes 144a. In addition, the measured gas can reach the sensor element 110 inside the inner protection cover 130 from the first gas chamber 122 through the first inner gas holes 134a. Furthermore, the first inner gas holes 134a and the first outer gas holes 144a are formed so that the first-inner-hole count Nin≥3, 0<the inner/outer hole count ratio Nr≤0.5, and 0<the inner/outer hole-area ratio Ar≤0.25. In this manner, since the number of the first outer gas holes 144a and the average area of the first outer gas holes 144a are relatively large, the flow rate of the measured gas flowing from the outside of the gas sensor 100 into the first gas chamber 122 is relatively high. In contrast, since the number of the first inner gas holes 134a and the average area of the first inner gas holes 134a are relatively small, the flow rate of the measured gas flowing from the first inner gas holes 134a into the inside of the inner protection cover 130 is relatively low. Thus, a decrease in the flow rate of the measured gas flowing from the first gas chamber 122 to the inside of the inner protection cover 130 is compensated by an increase in the flow rate of the measured gas flowing from the outside into the first gas chamber 122. Thus, an increase in the total time required for the measured gas flowing from the outside into the inside of the inner protection cover via the first gas chamber 122 can be prevented. That is, a decrease in the responsiveness of gas concentration detection can be prevented. In addition, since the flow rate of the measured gas flowing to the sensor element 110 (the flow rate of the measured gas flowing from the first gas chamber 122 into the inside of the inner protection cover 130) is regulated, the sensor element 110 is prevented from cooling. In this manner, the responsiveness of gas concentration detection of the gas sensor 100 and the high heat-retaining effect of the sensor element 110 can be obtained at the same time. Note that as the heat-retaining effect of the sensor element 110 is higher, a decrease in the sensitivity of detection of the gas concentration due to a decrease in the temperature can be more effectively prevented, and an increase in the power consumption of the heater that keeps the sensor element warm can be more effectively prevented.

Figure 11:
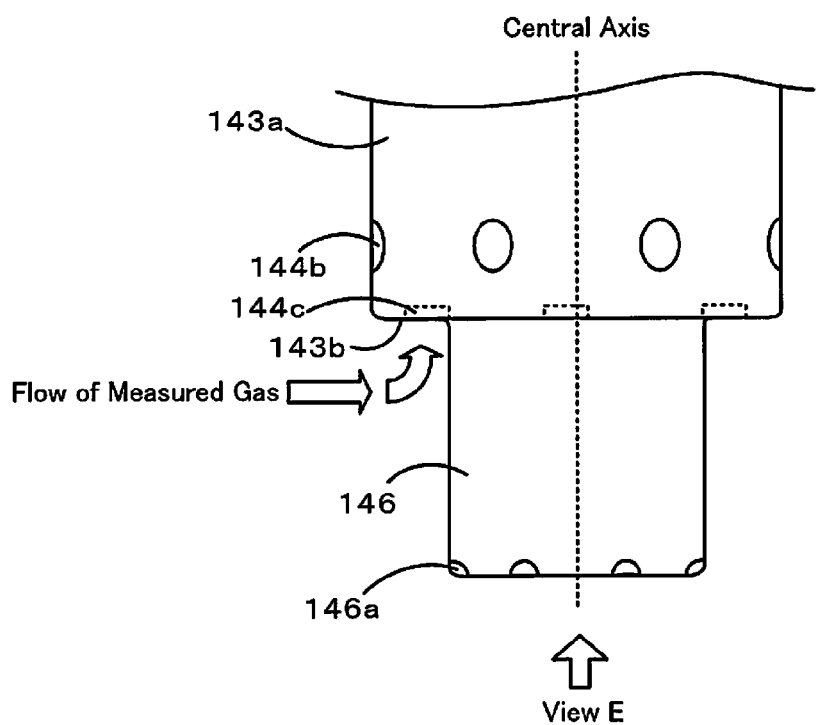
FIG. 11 illustrates the flow of the measured gas.
Figure 12:
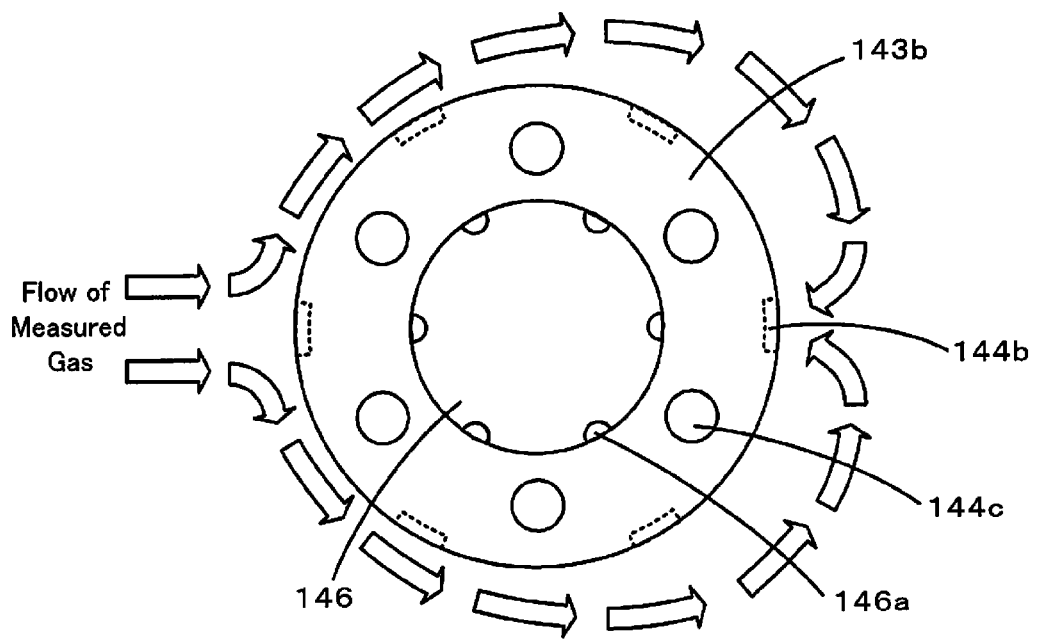
FIG. 12 is a view on Arrow E of FIG. 11.

In addition, the body portion 143 of the outer protection cover 140 includes the side portion 143a having a side surface extending in the direction of the central axis of the outer protection cover 140 and the stepped portion 143b that connects the side portion 143a to the tip end portion 146. The plurality of first outer gas holes 144a include at least three horizontal holes 144b formed in the side portion 143a of the outer protection cover 140 and at least three vertical holes 144c formed in the stepped portion 143b of the outer protection cover 140. In addition, the horizontal holes 144b are formed so that 0≤the horizontal hole non-existence maximum angle θhmax≤180°, and the vertical holes 144c are formed so that 0≤the vertical hole non-existence maximum angle θvmax≤180°. In this manner, the effect that increases the responsiveness of gas concentration detection can be reliably obtained. This effect is described in detail below. FIG. 11 illustrates the flow of the measured gas. FIG. 12 is a view on Arrow E of FIG. 11. Note that FIG. 11 illustrates the outer protection cover 140 viewed in a direction perpendicular to the direction of the flow of the measured gas when the measured gas flows from the left to the right of FIG. 2. As illustrated in FIG. 11, when the measured gas flows in a direction perpendicular to the central axis of the outer protection cover 140, the measured gas strikes the outer peripheral surface of the tip end portion 146 of the outer protection cover 140 in the upstream of the measured gas and, thus, a flow of the measured gas in the direction of the central axis is generated. Accordingly, the measured gas easily enters the vertical holes 144c located upstream of the outer protection cover 140. In addition, as illustrated in FIG. 12, since a gas flow that flows around the outer peripheral surface of the outer protection cover 140 is generated in the downstream of the measured gas, the measured gas easily enters the horizontal holes 144b. Accordingly, since the first outer gas holes 144a include the horizontal holes 144b and the vertical holes 144c, the flow rate of the measured gas from the outside into the first gas chamber 122 can be increased, and the responsiveness of gas concentration detection can be increased. In addition, by forming the horizontal holes and the vertical holes so that the following conditions are satisfied: the number of the horizontal holes is three or greater, the number of the vertical holes is three or greater, 0≤the horizontal hole non-existence maximum angle θhmax≤180°, and 0≤the vertical hole non-existence maximum angle θvmax≤180°, the vertical holes 144c can be easily located in the upstream of the measured gas, and the horizontal holes 144b can be easily located in the downstream of the measured gas even when the measured gas flows in any direction of the outer peripheral surface of the outer protection cover 140. That is, a change in the flow rate of the measured gas flowing from the outside into the first gas chamber 122 caused by the effect of the positional relationship between the direction in which the measured gas flows in the outside and the direction of the outer protection cover 140 can be prevented. In this manner, the effect that improves the responsiveness of gas concentration detection can be more reliably obtained. Note that when the gas sensor is manufactured, the direction in which the outer protection cover 140 is attached at the time of attaching the gas sensor to the pipe 20 is unknown. Accordingly, it is important to reduce the effect of the positional relationship between the direction in which the measured gas flows in the outside and the direction of the outer protection cover 140. The same can also apply to the positional relationship between the direction in which the measured gas flows and the direction of the inner protection cover 130 which is described in more detail below.

Furthermore, the horizontal holes 144b are formed so that the condition the horizontal hole non-existence maximum angle θhmax≤120° is satisfied, and the vertical holes 144c are formed so that the condition the vertical hole non-existence maximum angle θvmax≤120° is satisfied. Accordingly, a change in the flow rate of the measured gas flowing from the outside into the first gas chamber 122 caused by the effect of the positional relationship between the direction in which the measured gas flows in the outside and the direction of the outer protection cover 140 can be more effectively prevented. Still furthermore, the horizontal holes 144b are formed so that the condition the horizontal hole non-existence maximum angle θhmax≤(360°/the number of the horizontal holes) is satisfied, and the vertical holes 144c are formed so that the vertical hole non-existence maximum angle θvmax≤(360°/the number of the vertical holes). Accordingly, the change in the flow rate of the measured gas flowing from the outside into the first gas chamber 122 caused by the effect of the positional relationship between the direction in which the measured gas flows in the outside and the direction of the outer protection cover 140 can be more effectively prevented. In addition, when the horizontal holes 144b are projected onto a plane that is perpendicular to the central axis of the outer protection cover 140, the horizontal holes 144b are arranged along the circumferential direction of the outer protection cover 140 at equal intervals. Accordingly, the arrangement and the sizes of the areas in which the horizontal holes 144b do not consecutively exist as viewed in the circumferential direction of the outer protection cover 140 (i.e., the horizontal hole non-existence areas) are not biased. As a result, a change in the flow rate of the measured gas flowing from the outside into the first gas chamber 122 caused by the effect of the direction of the outer protection cover 140 can be more effectively prevented. Similarly, the vertical holes 144c are arranged in the circumferential direction of the outer protection cover 140 at equal intervals, the arrangement and the sizes of the vertical hole non-existence areas are not biased. As a result, a change in the flow rate of the measured gas flowing from the outside into the first gas chamber 122 caused by the effect of the direction of the outer protection cover 140 can be more effectively prevented. Furthermore, the horizontal holes 144b and the vertical holes 144c are arranged so that the distance between a horizontal hole 144b and a neighboring vertical hole 144c in the circumferential direction is the same for all the horizontal holes 144b and vertical holes 144c. This further prevents a change in the flow rate of the measured gas flowing from the outside into the first gas chamber 122 caused by the effect of the direction of the outer protection cover 140 can be more effectively prevented.

Furthermore, the first inner gas holes 134a are formed so that the first-inner-hole count Nin≥3 and 0≤the first-inner-hole non-existence maximum angle θinmax≤120°. The first outer gas holes 144a are formed so that the first-outer-hole count Nout≥6 and 0≤the first-outer-hole non-existence maximum angle θoutmax≤60°. Accordingly, a change in the flow rate of the measured gas flowing from the outside into the first gas chamber and a change in the flow rate of the measured gas flowing from the first gas chamber into the inner protection cover caused by the effect of the positional relationship between the direction in which the measured gas flows in the outside and each of the directions of the outer protection cover and the inner protection cover can be more effectively prevented. Furthermore, the first inner gas holes 134a and the first outer gas holes 144a are formed so that the conditions the first-inner-hole non-existence maximum angle θinmax≤(360°/the first-inner-hole count Nin) and the first-outer-hole non-existence maximum angle θoutmax≤(360°/the first-outer-hole count Nout) are satisfied. Accordingly, a change in the flow rate of the measured gas flowing into the first gas chamber and a change in the flow rate of the measured gas flowing from the first gas chamber into the sensor element chamber 124 can be more effectively prevented.

Still furthermore, the first outer gas holes 144a are formed so that each of the opening areas thereof is 0.196 mm$^2$ to 3.14 mm$^2$. Accordingly, an unwanted component in the measured gas, such as a water droplet or soot, entering the inside of the outer protection cover 140 through the first outer gas holes 144a can be more effectively prevented. If a water droplet enters the outer protection cover 140, the water droplet may reach the sensor element 110 and, thus, the sensor element 110 may be cracked. The above-described configuration can prevent such crack. In addition, if soot enters the inside of the outer protection cover 140, the holes, such as the first inner gas holes 134a, may be clogged. The above-described configuration can prevent such clogging. Furthermore, if the soot is deposited onto, for example, the inner protection cover 130, the soot easily receives the heat of radiation from the sensor element 110 and, thus, the temperature of the sensor element 110 easily decreases. The above-described configuration can prevent such a decrease in temperature.

Yet still furthermore, since the opening area of each of the first inner gas holes 134a is greater than or equal to 0.2 mm², clogging of the first inner gas holes due to an unwanted component, such as a soot, in the measured gas can be more effectively prevented.

Yet still furthermore, the central point of the opening of each of the first inner gas holes 134a is located 5 mm or more away from the front end of the sensor element 110 towards the rear end of the sensor element 110. The measured gas that has entered the sensor element chamber 124 from the first inner gas holes 134a flows into the second gas chamber 126 through the second inner gas holes 138a formed at a position further away in the tip direction of the sensor element 110 than the first inner gas hole 134a. Accordingly, it is difficult for the measured gas to reach the space closer to the rear end of the sensor element 110 (the opposite side from the second gas chamber 126) than the first inner gas hole 134a. Thus, the time required for replacing the space of the sensor element chamber 124 with the measured gas increases, and the responsiveness of gas concentration detection may decrease. By placing the central point of the opening of the first inner gas hole 134a at a point 5 mm or more away from the tip end of the sensor element 110 towards the rear end of the sensor element 110, the measured gas is allowed to easily reach the space on the rear side of the sensor element 110 and, thus, a decrease in the responsiveness of gas concentration detection can be more effectively prevented.

It should be noted that the present invention is not limited to the above-described embodiment in any way, and a variety of modifications can be made without departing from the spirit and the technical scope of the invention.

Figure 13:
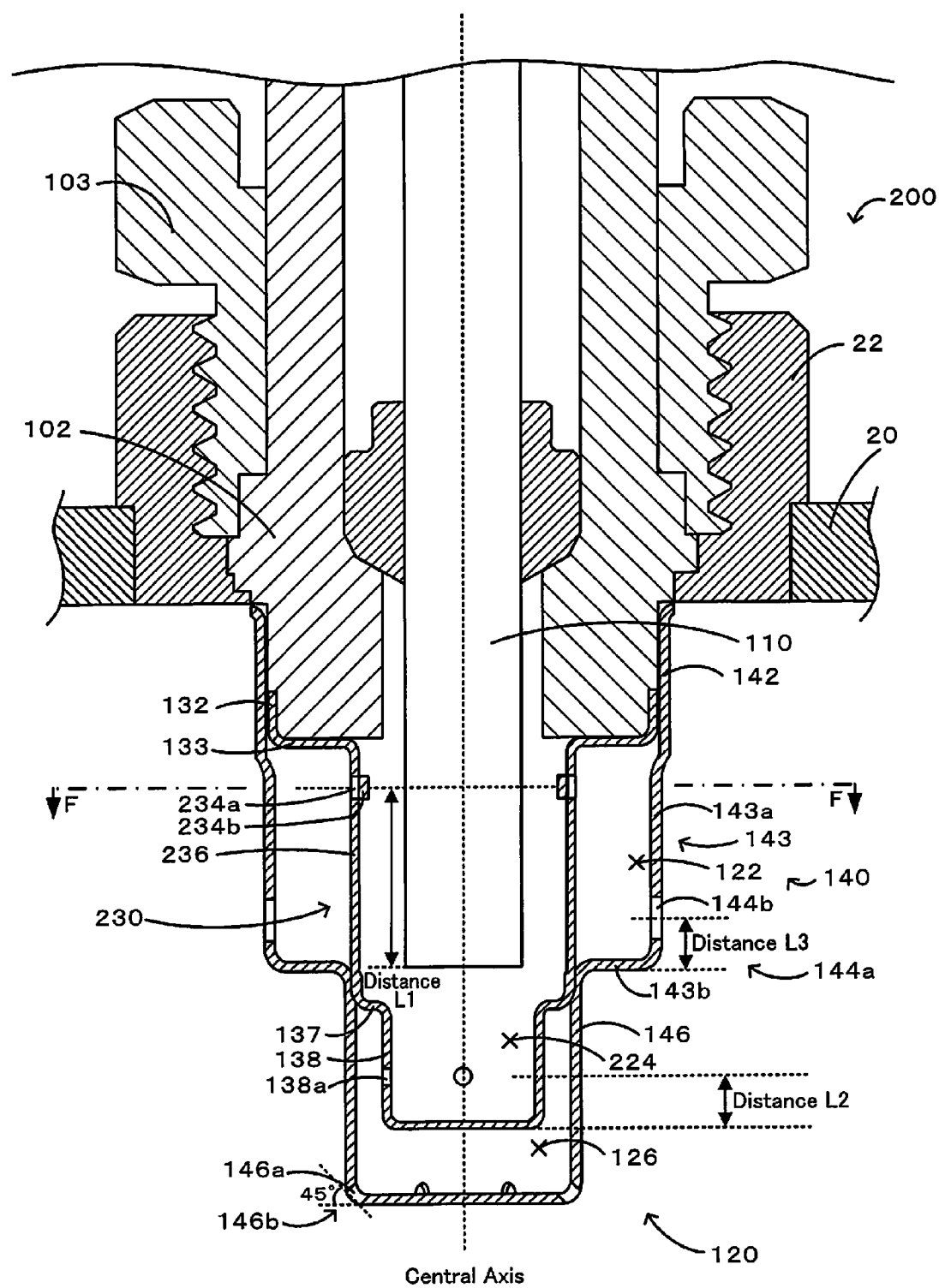
FIG. 13 is a vertical cross-sectional view of a gas censor 200 according a modification.
Figure 14:
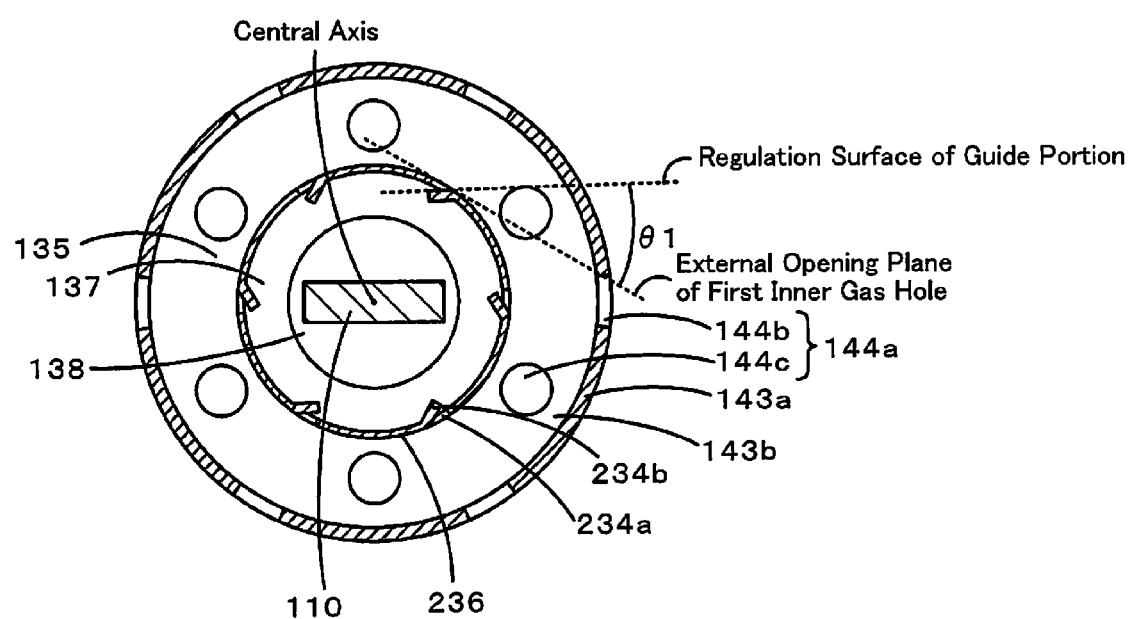
FIG. 14 is a cross-sectional view taken along a line F-F of FIG. 13.

For example, while the above embodiment has been described with reference to the inner protection cover 130 including the first body portion 134, the stepped portion 135, and the second body portion 136, the stepped portion 135 may be removed, and the inner diameters of the first body portion 134 and the second body portion 136 may be made the same. FIG. 13 is a vertical cross-sectional view of a gas censor 200 according a modification. FIG. 14 is a view on Arrow F of FIG. 13. Note that in FIGS. 13 and 14, constituent elements similar to those of the gas sensor 100 are identified with the same reference numeral, and detailed description of the constituent elements is not repeated. As illustrated in FIG. 13, in the gas censor 200, the inner protection cover 230 includes a body portion 236 instead of including the first body portion 134, the stepped portion 135, and the second body portion 136. The body portion 236 is connected to the large-diameter portion 132 via the stepped portion 133. The body portion 236 is connected to the tip end portion 138 via the stepped portion 137. The body portion 236 has a length in the vertical direction in FIG. 13 that is the same as the sum of the lengths of the first body portion 134, the stepped portion 135, and the second body portion 136 in the vertical direction in FIG. 2. In addition, the body portion 236 has an inner diameter that is the same as that of the second body portion 136 illustrated in FIG. 2. That is, the shape of the inner protection cover 230 corresponds to a shape of the first body portion 134 of the inner protection cover 130 illustrated in FIG. 2 having a diameter that is the same as the inner diameter of the second body portion 136. According to such a configuration, the space inside the inner protection cover 230, that is, the volume of a sensor element chamber 224 is made smaller than that of the sensor element chamber 124 illustrated in FIG. 2. By reducing the volume of the sensor element chamber 224 in this manner, the time required for replacing the space of the sensor element chamber 224 with the measured gas can be reduced and, thus, the responsiveness of concentration detection can be increased. Note that as illustrated in FIG. 14, in the gas censor 200, six first inner gas holes 234a are formed in the body portion 236 at equal intervals, and six guide portions 234b are formed in the body portion 236 at equal intervals. The plurality of guide portions 234b are formed so as to be rotationally symmetrical (sixfold rotationally symmetrical). The first inner gas hole 234a and the guide portion 234b have configurations that are the same as those of the first inner gas hole 134a and the guide portion 134b of the gas sensor 100, respectively, except for the numbers thereof.

Figure 15:
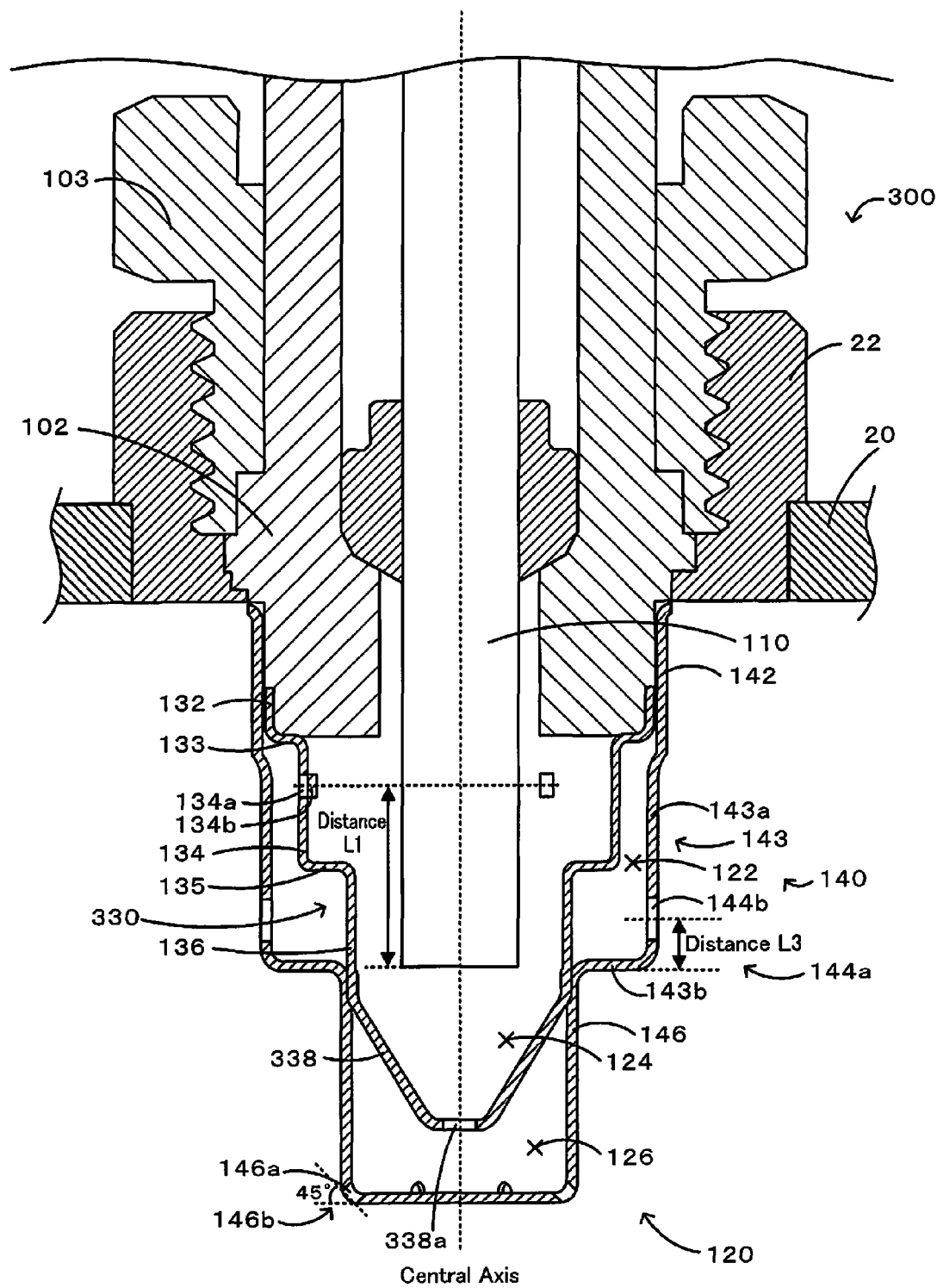
FIG. 15 is a vertical cross-sectional view of a gas sensor 300 according to a modification.

The shape of the protection cover is not limited to that illustrated in FIGS. 2 and 13. A protection cover having another shape may be employed. FIG. 15 is a vertical cross-sectional view of a gas sensor 300 according to a modification. Note that in FIG. 15, constituent elements similar to those of the gas sensor 100 are identified with the same reference numeral, and detailed description of the constituent elements is not repeated. As illustrated in FIG. 15, the gas censor 300 includes an inner protection cover 330. The inner protection cover 330 has a configuration that is similar to the configuration of the inner protection cover 130 illustrated in FIG. 2 except that the shapes of a tip end portion 338 and a second inner gas hole 338a differ from the shapes of the tip end portion 138 and the second inner gas hole 138a, respectively, and the stepped portion 137 is removed. Unlike the tip end portion 138, the tip end portion 338 has a shape obtained by turning a truncated triangular pyramid upside down. The tip end portion 338 is connected to the second body portion 136. In addition, the second inner gas hole 338a is a circular hole located at the central point of the bottom surface of the tip end portion 338.

While the above embodiment has been described with reference to three first inner gas holes 134a and 12 first outer gas holes 144a, the numbers are not limited thereto. In addition, the positions and the opening areas of the first inner gas holes 134a and the first outer gas holes 144a are not limited to those in the above-described embodiment. It is only required that the first inner gas holes 134a and the first outer gas holes 144a are formed so that the first-inner-hole count Nin≥3, 0<the inner/outer hole count ratio Nr≤0.5, and 0<the inner/outer hole-area ratio Ar≤0.25. For example, the opening area of at least one of the first outer gas holes 144a may be outside the range from 0.196 mm² to 3.14 mm². In addition, the opening area of at least one of the first inner gas holes 134a may be less than 0.2 mm². Alternatively, the opening areas of all the first inner gas holes 134a need not be the same. However, it is desirable that the opening area of each of the plurality of first inner gas holes 134a be in the range from 0.8 times to 1.2 times the first-inner-hole average area Ain. The shape of the opening of the first inner gas hole 134a is not limited to a rectangle. For example, the shape may be an exact circle, an ellipse, or a polygon. In addition, the guide portions 134b may be removed from the configuration. The opening areas of all the plurality of first outer gas holes 144a need not be the same. However, it is desirable that the opening area of each of the plurality of first outer gas holes 144a be in the range from 0.8 times to 1.2 times the first-outer-hole average area Aout. The shape of the opening of the first outer gas hole 144a is not limited to the exact circle. For example, the shape may be another shape, such as an ellipse or a polygon.

According to the above-described embodiment, the gas sensor 100 satisfies the following conditions: the first-inner-hole count Nin≥3, 0≤the first-inner-hole non-existence maximum angle θinmax≤120°, the first-outer-hole count Nout≥6, and 0≤the first-outer-hole non-existence maximum angle θoutmax≤60°. However, the conditions are not limited thereto. For example, the gas sensor 100 may satisfy the following condition: the first-inner-hole count Nin≥3, 0≤the first-inner-hole non-existence maximum angle θinmax≤180°, the first-outer-hole count Nout≥6, and 0≤the first-outer-hole non-existence maximum angle θoutmax≤90°. Alternatively, the gas sensor 100 need not satisfy these conditions. However, to more reliably obtain the effect that increases the responsiveness of gas concentration detection, it is desirable that the following conditions be satisfied: the first-inner-hole count Nin≥3, 0≤the first-inner-hole non-existence maximum angle θinmax≤180°, the first-outer-hole count Nout≥6, and 0≤the first-outer-hole non-existence maximum angle θoutmax≤90°. In addition, it is more desirable that the following conditions be satisfied: the first-inner-hole non-existence maximum angle θinmax≤120° and the first-outer-hole non-existence maximum angle θoutmax≤60°.

While the above embodiment has been described with reference to the conditions the horizontal hole non-existence angles θh1 to θh6 that are the same and 0≤the horizontal hole non-existence maximum angle θhmax<60° (=360°/the number of the horizontal holes 144b), the horizontal hole non-existence angles θh1 to θh6 need not be the same if the condition 0<the horizontal hole non-existence maximum angle θhmax≤(360°/the number of the horizontal holes 144b) is satisfied. The same applies to the vertical hole non-existence angles θv1 to θv6, the first-outer-hole non-existence angles θout1 to θout12, and the first-inner-hole non-existence angles θin1 to θin3. In addition, the condition 0<the horizontal hole non-existence maximum angle θhmax≤(360°/the number of the horizontal holes 144b) need not be satisfied. The same applies to the vertical hole non-existence maximum angle θvmax, the first-outer-hole non-existence maximum angle θoutmax, and the first-inner-hole non-existence maximum angle θinmax.

While the above embodiment has been described with reference to the first outer gas holes 144a including six horizontal holes 144b and six vertical holes 144c, the number of the horizontal holes 144b and the number of the vertical holes 144c are not limited thereto. For example, the number of the horizontal holes 144b may differ from the number of the vertical holes 144c. Alternatively, the first outer gas holes 144a may include only the horizontal holes 144b or only the vertical holes 144c. Note that if the first outer gas holes 144a include only the horizontal holes 144b, the horizontal hole non-existence maximum angle θhmax=the first-outer-hole non-existence maximum angle θoutmax. Similarly, if the first outer gas holes 144a include only the vertical holes 144c, the vertical hole non-existence maximum angle θmax=the first-outer-hole non-existence maximum angle θoutmax. Alternatively, in addition to or instead of the horizontal holes 144b and the vertical holes 144c, the first outer gas holes 144a may include holes formed in a corner portion which is a boundary portion between the side portion 143a and the stepped portion 143b of the body portion 143.

While the above embodiment has been described with reference to each of the second inner gas holes 138a and the second outer gas holes 146a each having a cross-sectional shape perpendicular to the central axis thereof being an exact circle, the cross-sectional shape is not limited thereto. For example, the cross-sectional shape perpendicular to the central axis may be an ellipse or a polygon (e.g., a rectangle). In addition, the arrangements and the numbers of the second inner gas holes 138a and the second outer gas holes 146a are not limited to those of the above-described embodiment. For example, while the above embodiment has been described with reference to the second outer gas holes 146a formed in the corner portion 146b which is a boundary portion between the side surface and the bottom surface of the tip end portion 146, the portion in which the second outer gas holes 146a are formed is not limited to the corner portion 146b. For example, the second outer gas holes 146a may be formed in the side surface or the bottom surface. The second outer gas holes may include at least one hole formed in at least one of the corner portion 146b, the side surface, and the bottom surface. The second outer gas holes may include at least three horizontal holes formed in the side surface of the tip end portion 146 and at least three vertical holes formed in the bottom surface of the tip end portion 146. The intervals of the plurality of second outer gas holes 146a may or may not be equal intervals in the circumferential direction of the outer protection cover 140.

While the above embodiment has been described with reference to the distance L1 between the tip end of the sensor element 110 and the central point of the opening of the first inner gas hole 134a being 5 mm or greater, the distance L is not limited thereto. The distance may be less than 5 mm. For example, the first inner gas holes 134a may be formed in the second body portion 136. In addition, the first inner gas holes 134a may be formed at positions further away in the tip direction of the sensor element 110 than the tip end of the sensor element 110 (the downward direction of FIG. 2).

EXAMPLES

Experimental Example 1

The gas sensor 100 illustrated in FIGS. 2 to 12 serves as Experimental Example 1. More specifically, the inner protection cover 130 is 0.3 mm in thickness and is 17.7 mm in length in the axial direction. The large-diameter portion 132 is 1.8 mm in length in the axial direction. The first body portion 134 is 5.4 mm in length in the axial direction. The second body portion 136 is 5.6 mm in length in the axial direction. The tip end portion 138 is 4.9 mm in length in the axial direction. The external diameter of the large-diameter portion 132 is 14.1 mm. The external diameter of the first body portion 134 is 11.8 mm. The external diameter of the second body portion 136 is 8.2 mm. The external diameter of the tip end portion 138 is 5.9 mm. The first-inner-hole count Nin of the first inner gas holes 134a is 3. The first-inner-hole average area Ain is 0.200 mm². The distance L1 is 6 mm. The first-inner-hole non-existence maximum angle θinmax is 115°. The formed angle θ1 is 38°. The inner diameter of the second inner gas hole 138a is 1.0 mm. The number of the second inner gas holes 138a is 4. The distance L2 is 1.1 mm. Note that the three first inner gas holes 134a have the same size (each of the opening areas is 0.200 mm²). In addition, the outer protection cover 140 is 0.4 mm in thickness and is 24.2 mm in length in the axial direction. The large-diameter portion 142 is 6.1 mm in length in the axial direction. The body portion 143 is 8.5 mm in length in the axial direction. The tip end portion 146 is 9.6 mm in length in the axial direction. The external diameter of the large-diameter portion 142 is 15.2 mm. The external diameter of the body portion 143 is 14.6 mm. The external diameter of the tip end portion 146 is 8.7 mm. The first-outer-hole count Nout of the first outer gas holes 144a is 12 (the number of the horizontal holes 144b is 6, and the number of the vertical holes 144c is 6). The distance L3 is 1.5 mm. The diameter of each of the first outer gas holes 144a is 1 mm (the opening area is 0.785 mm²). The first-outer-hole average area Aout is 0.785 mm². The horizontal hole non-existence maximum angle θhmax is 49°. The vertical hole non-existence maximum angle θvmax is 47°. The first-outer-hole non-existence maximum angle θoutmax is 19°. The inner diameter of the second outer gas hole 146a is 1.2 mm. The number of the second outer gas holes 146a is 6. The angle 92 formed by the second outer gas hole 146a is 45°. Note that the first inner gas holes 134a are formed at equal intervals, the second inner gas holes 138a are formed at equal intervals, the first outer gas holes 144a are formed at equal intervals, and the second outer gas holes 146a are formed at equal intervals. The inner/outer hole count ratio Nr of the gas sensor 100 of Experimental Example 1 is 0.25, and the inner/outer hole-area ratio Ar is 0.25. In addition, the sensor element 110 of the gas sensor 100 detects the oxygen concentration.

Experimental Examples 2 to 12

Figure 16:
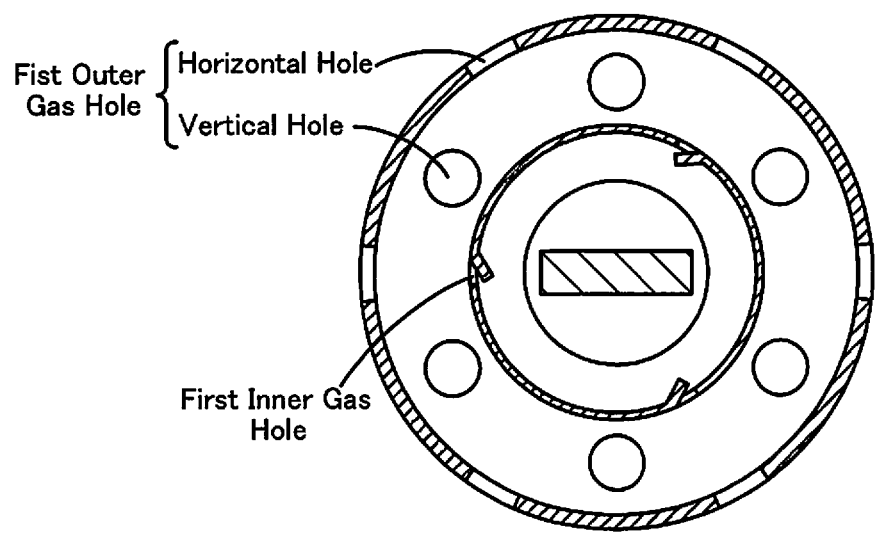
FIG. 16 is a cross-sectional view illustrating the arrangement of the first inner gas holes and the first outer gas holes of Experimental Example 3.

Experimental Examples 2 to 11 are configured by changing the values of the first-outer-hole count Nout, the first-inner-hole count Nin, the inner/outer hole count ratio Nr, the first-outer-hole average area Aout, the first-inner-hole average area Ain, the inner/outer hole-area ratio Ar, the horizontal hole non-existence maximum angle θhmax, the vertical hole non-existence maximum angle θvmax, the first-outer-hole non-existence maximum angle θoutmax, the first-inner-hole non-existence maximum angle θinmax, and the distance L1 of the gas sensor of Experimental Example 1 to those indicated by Table 1. More specifically, Experimental Example 2 is configured as follow. That is, the shape of the inner protection cover is changed into the shape of the inner protection cover 230 of the gas censor 200 illustrated in FIGS. 13 and 14. The first-inner-hole count Nin=6. The inner/outer hole count ratio Nr=0.5. The first-inner-hole non-existence maximum angle θinmax=55°. The other values are the same as those of the gas sensor of Experimental Example 1. In addition, Experimental Example 3 is configured as follows. That is, the first-inner-hole count Nin=3. The inner/outer hole count ratio Nr=0.25. The first-inner-hole non-existence maximum angle θinmax=115°. The other values are the same as those of the gas sensor of Experimental Example 2. FIG. 16 is a cross-sectional view illustrating the arrangement of the first inner gas holes and the first outer gas holes of Experimental Example 3.

Figure 17:
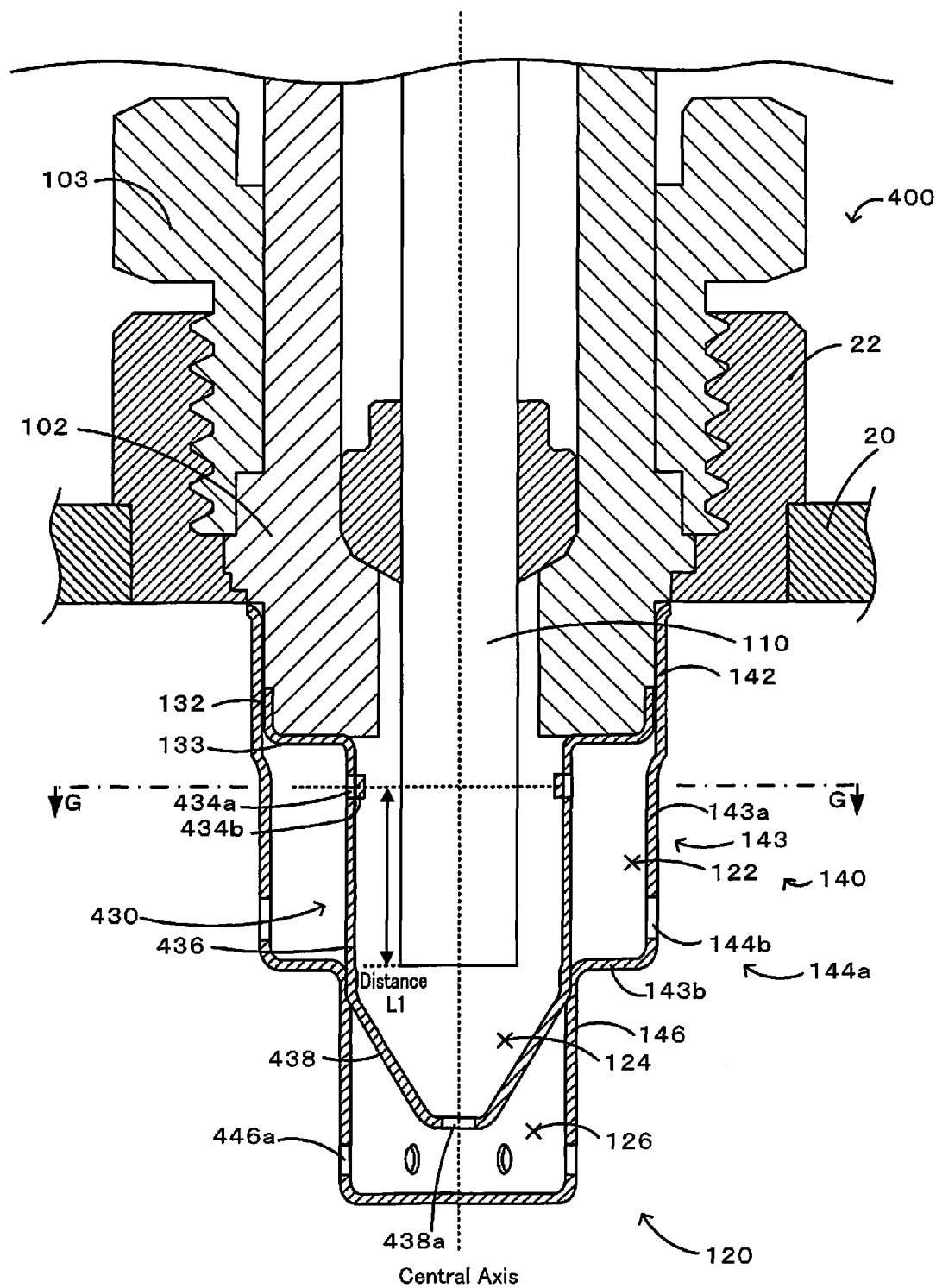
FIG. 17 is a vertical cross-sectional view of the gas sensor 400 according to Experimental Example 4.
Figure 18:
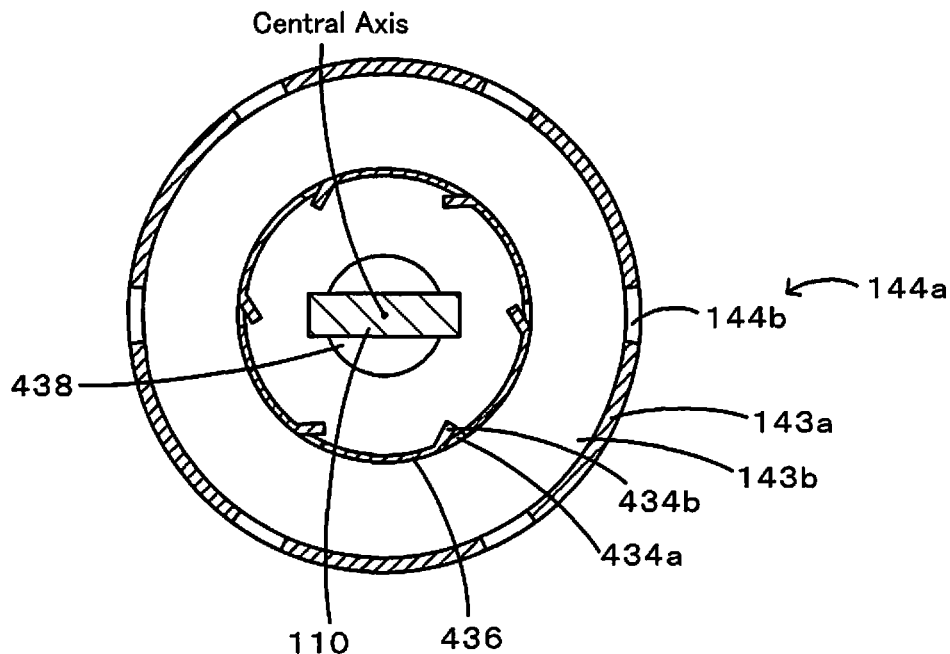
FIG. 18 is a cross-sectional view taken along a line G-G of FIG. 17.

A gas sensor 400 illustrated in FIGS. 17 and 18 serves as Experimental Example 4. FIG. 17 is a vertical cross-sectional view of the gas sensor 400 according to Experimental Example 4. FIG. 18 is a cross-sectional view taken along a line G-G of FIG. 17. In FIGS. 17 and 18, constituent elements similar to those of the gas sensor 100 are identified with the same reference numeral, and detailed description of the constituent elements is not repeated. As illustrated in FIG. 17, the gas sensor 400 includes an inner protection cover 430. Instead of including the first body portion 134, the stepped portion 135, the second body portion 136, and the tip end portion 138, the inner protection cover 430 includes a body portion 436 and a tip end portion 438. The body portion 436 has a structure that is the same as the structure of the body portion 236 illustrated in FIG. 13. The body portion 436 is connected to the large-diameter portion 132 via the stepped portion 133. The body portion 436 is connected to the tip end portion 438. The tip end portion 438 has a structure that is the same as the structure of the tip end portion 338 illustrated in FIG. 15. The tip end portion 438 has second inner gas holes 438a formed therein. The second inner gas holes 438a are similar to the second inner gas holes 338a. In addition, the body portion 436 has six first inner gas holes 434a formed therein at equal intervals and six guide portions 434b formed therein at equal intervals (refer to FIG. 18). The structures of the first inner gas hole 434a and the guide portion 434b are the same as those of the first inner gas hole 234a and the guide portion 234b illustrated in FIG. 14, respectively. In addition, instead of the second outer gas holes 146a, the gas sensor 400 has six second outer gas holes 446a formed in the side surface of the tip end portion 146 at equal intervals (refer to FIG. 17). Each of the second outer gas holes 446a has a circular opening. The diameter of the second outer gas hole 446a is 1.2 mm. The first outer gas holes 144a do not include the vertical holes 144c and, thus, the first-outer-hole count Nout=6 (the number of the horizontal holes 144b is 6). The diameter of each of the six first outer gas holes 144a is 1 mm (the opening area of each of the first outer gas holes 144a is 0.785 mm²). The six first inner gas holes 434a have the same size. More specifically, the opening area of each of the first inner gas holes 434a is 0.479 mm² (the first-inner-hole average area Ain=0.479 mm²). In addition, the inner/outer hole count ratio Nr=1. The inner/outer hole-area ratio Ar=0.61. The horizontal hole non-existence maximum angle θhmax=47°. The vertical hole non-existence maximum angle θvmax=360° (there are no vertical holes 144c). The first-outer-hole non-existence maximum angle θoutmax=47° (the same value as the value of the horizontal hole non-existence maximum angle θhmax). The first-inner-hole non-existence maximum angle θinmax=52°. The distance L1=6 mm.

Figure 19:
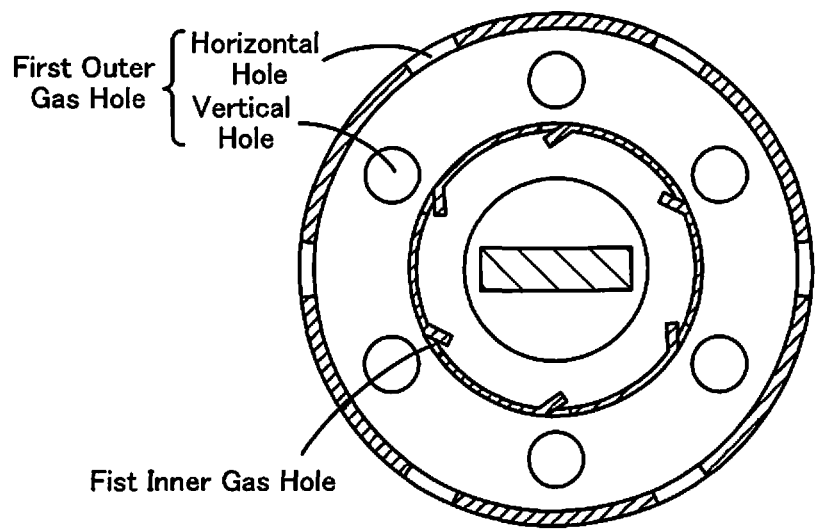
FIG. 19 is a cross-sectional view illustrating the arrangement of the first inner gas holes and the first outer gas holes of Experimental Example 8.

The following gas sensor is configured as Experimental Example 5. That is, the first-outer-hole count Nout=6 (the number of holes formed in the boundary portion between the side portion 143a and the stepped portion 143b is 6). The first-inner-hole count Nin=6. The first-inner-hole average area Ain=0.396 me. The inner/outer hole count ratio Nr=1. The inner/outer hole-area ratio Ar=0.50. The horizontal hole non-existence maximum angle θhmax=360° (there is no horizontal holes 144b). The vertical hole non-existence maximum angle θvmax=360° (there is no vertical holes 144c). The first-outer-hole non-existence maximum angle θoutmax=49°. The first-inner-hole non-existence maximum angle θinmax=53°. The other values are the same as those of Experimental Example 1. Note that in Experimental Example 5, the six first inner gas holes 134a have the same size, and each of the opening areas is 0.396 mm². The following gas sensor is configured as Experimental Example 6. That is, the first-inner-hole count Nin=6. The first-inner-hole average area Ain=0.396 mm². The inner/outer hole count ratio Nr=0.5. The inner/outer hole-area ratio Ar=0.50. The first-inner-hole non-existence maximum angle θinmax=53°. The other values are the same as those of Experimental Example 1. Note that in Experimental Example 6, the six first inner gas holes 134a have a size that is the same as that of Experimental Example 5. The following gas sensor is configured as Experimental Example 7. That is, the shape of the inner protection cover is the same as the shape illustrated in FIG. 13. The first-inner-hole non-existence maximum angle θinmax=52°. The other values are the same as those of Experimental Example 6. Note that the arrangement of the first inner gas holes and the first outer gas holes of Experimental Example 7 is the same as that illustrated in FIG. 14. The following gas sensor is configured as Experimental Example 8. That is, the position at which the inner protection cover is attached is rotated about the central axis of the gas sensor by 30°. The other values are the same as those of Experimental Example 7. The arrangement of the first inner gas holes and the first outer gas holes of Experimental Example 8 is illustrated in FIG. 19. The following gas sensor is configured as Experimental Example 9. That is, the first-inner-hole average area Ain=0.277 mm². The inner/outer hole-area ratio Ar=0.35. The first-inner-hole non-existence maximum angle θinmax=54°. The other values are the same as those of Experimental Example 7. Note that in Experimental Example 9, the six first inner gas holes 134a have the same size, and each of the opening areas is 0.277 mm². The following gas sensor is configured as Experimental Example 10. That is, the first-inner-hole count Nin=3. The inner/outer hole count ratio Nr=0.25. The first-inner-hole non-existence maximum angle θinmax=112°. The other values are the same as those of Experimental Example 7. Note that the arrangement of the first inner gas holes and the first outer gas holes of Experimental Example 10 is the same as that illustrated in FIG. 16. The following gas sensor is configured as Experimental Example 11. That is, the distance L1=3 mm. The other values are the same as those of Experimental Example 3. Note that in Experimental Examples 2 to 11, the first inner gas holes are formed at equal intervals, and the first outer gas holes are formed at equal intervals.

[Evaluation Test 1]

The gas sensors of Experimental Examples 1 to 11 were evaluated in terms of the heat-retaining effect and the responsiveness of gas concentration detection of the sensor element. The result of the evaluation is shown in Table 1. More specifically, the evaluation was conducted as follows.

That is, each of the gas sensors of Experimental Examples 1 to 11 was attached to a pipe in the same manner as illustrated in FIG. 1. Note that the pipe was completely filled with air. The pipe was kept with the inside under windless conditions for 310 seconds. Thereafter, the measured gas was moved through the pipe at a predetermined flow velocity of V. Note that in Experimental Example 1, the measured gas was moved from the left to the right in FIGS. 2 and 3. The same applied to Experimental Examples 2 to 11. At that time, a variation of the output of the sensor element with time was measured. It was assumed that the air in the inner protection cover was completely replaced with the measured gas when the output of the sensor element was maximized. The ratio of the output of the sensor element to the highest value was obtained as a gas replacement ratio for the inside of the inner protection cover. Thus, the variation of the gas replacement ratio with time was obtained. The predetermined flow velocity V of the measured gas was set to 30 m/s, and the variation of the gas replacement ratio with time was obtained. Thereafter, an elapsed time from when the measured gas started to be moved to when the gas replacement ratio exceeds 90% was defined as a response time of gas concentration detection. In addition, an average flow rate of the measured gas that flowed from the first gas chamber to the sensor element chamber during the time period from when the measured gas started to be moved to when the gas replacement ratio exceeds 90% was measured. The value was defined as a mass flow rate Fin (kg/s) of the gas flowing into the sensor element chamber. If the mass flow rate Fin is lower than $2.92 \times 10^{-5}$ kg/s, it is determined that the heat-retaining effect is fair (a circle). If the mass flow rate Fin is lower than $2.00 \times 10^{-5}$ kg/s, it is determined that the heat-retaining effect is excellent (a double circle). Note that the heat-retaining effect of the sensor element increases with decreasing mass flow rate Fin. In addition, if the response time is less than or equal to 0.30 seconds, it is determined that the responsiveness is fair (a circle). If the response time is less than or equal to 0.20 seconds, it is determined that the responsiveness is excellent (a double circle). Note that the responsiveness of gas concentration detection increases with decreasing response time.

TABLE 1

| Experimental Examples | Hole Count First-Outer-Hole Count Nout | Hole Count First-Inner-Hole Count Nin | Inner/Outer Hole Cout Ratio Nr | Area First-Outer-Hole Average Area Aout (mm²) | Area First-Inner-Hole Average Area Ain (mm²) | Inner/Outer Hole-Area Ratio Ar | Horizontal Hole Non-Existence Maximum Angle θ hmax (°) | Vertical Hole Non-Existence Maximum Angle θ vmax (°) | First-Outer-Hole Non-Existence Maximum Angle θ outmax (°) |
|---|---|---|---|---|---|---|---|---|---|
| 1 | 12 | 3 | 0.25 | 0.785 | 0.200 | 0.25 | 49 | 47 | 19 |
| 2 | 12 | 6 | 0.5 | 0.785 | 0.200 | 0.25 | 49 | 47 | 19 |
| 3 | 12 | 3 | 0.25 | 0.785 | 0.200 | 0.25 | 49 | 47 | 19 |
| 4 | 6 | 6 | 1 | 0.785 | 0.479 | 0.61 | 47 | 360 | 47 |
| 5 | 6 | 6 | 1 | 0.785 | 0.396 | 0.50 | 360 | 360 | 49 |
| 6 | 12 | 6 | 0.5 | 0.785 | 0.396 | 0.50 | 49 | 47 | 19 |
| 7 | 12 | 6 | 0.5 | 0.785 | 0.396 | 0.50 | 49 | 47 | 19 |
| 8 | 12 | 6 | 0.5 | 0.785 | 0.396 | 0.50 | 49 | 47 | 19 |
| 9 | 12 | 6 | 0.5 | 0.785 | 0.277 | 0.35 | 49 | 47 | 19 |
| 10 | 12 | 3 | 0.25 | 0.785 | 0.396 | 0.50 | 49 | 47 | 19 |
| 11 | 12 | 3 | 0.25 | 0.785 | 0.200 | 0.25 | 49 | 47 | 19 |

TABLE 1-continued

| | First- Inner- Hole Non- Existence | | Test of Heat-Retaining Effect and Responsiveness (Row Velocity of V = 30 m/s) | | | |
|---|---|---|---|---|---|---|
| | | | Heat-Retaining Effect | | | |
| | Maximum | | Mass | | Responsiveness | |
| Experimental Examples | Angle θ inmax (°) | Distance L1 (mm) | Flow Rate Fin(kg/s) | Evaluation | Response Time (sec) | Evaluation |
| 1 | 115 | 6.0 | 2.70E−05 | ○ | 0.22 | ○ |
| 2 | 55 | 6.0 | 2.85E−05 | ○ | 0.16 | ⊚ |
| 3 | 115 | 6.0 | 1.68E−05 | ⊚ | 0.25 | ○ |
| 4 | 52 | 6.0 | 1.23E−05 | ⊚ | 0.34 | X |
| 5 | 53 | 6.0 | 2.92E−05 | X | 0.25 | ○ |
| 6 | 53 | 6.0 | 4.34E−05 | X | 0.14 | ⊚ |
| 7 | 52 | 6.0 | 4.77E−05 | X | 0.11 | ⊚ |
| 8 | 52 | 6.0 | 4.87E−05 | X | 0.11 | ⊚ |
| 9 | 54 | 6.0 | 3.84E−05 | X | 0.13 | ⊚ |
| 10 | 112 | 6.0 | 3.09E−05 | X | 0.16 | ⊚ |
| 11 | 115 | 3.0 | 1.68E−05 | ⊚ | 0.30 | ○ |

As can be seen from Table 1, Experimental Examples 1 to 3 and 11 that satisfy the conditions the first-inner-hole count Nin≥3, 0<the inner/outer hole count ratio Nr≤0.5, and 0<the inner/outer hole-area ratio Ar≤0.25 provide a result of "Fair" for each of the high heat-retaining effect and the responsiveness. In contrast, Experimental Examples 4 to 10 that do not satisfy any one of the conditions the first-inner-hole count Nin≥3, 0<the inner/outer hole count ratio Nr≤0.5, and the 0<the inner/outer hole-area ratio Ar≤0.25 provide a result of "Poor" for one of the heat-retaining effect and the responsiveness. In addition, comparison of Experimental Example 3 and Experimental Example 11 having the same conditions except for the distance L1 indicates that Experimental Example 3 having the distance L1 greater than or equal to 5 mm exhibits higher responsiveness. Furthermore, Experimental Example 3 and Experimental Example 11 have the same heat-retaining effect.

Experimental Examples 12 to 13

Figure 20:
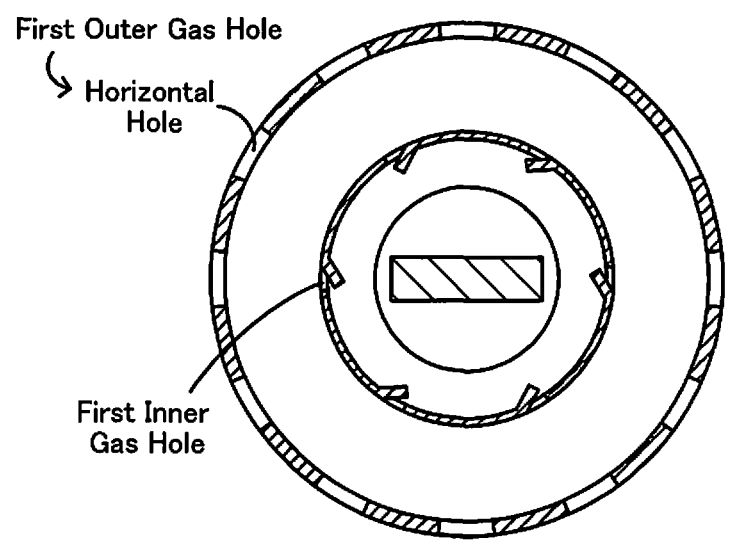
FIG. 20 is a cross-sectional view illustrating the arrangement of the first inner gas holes and the first outer gas holes of Experimental Example 12.
Figure 21:
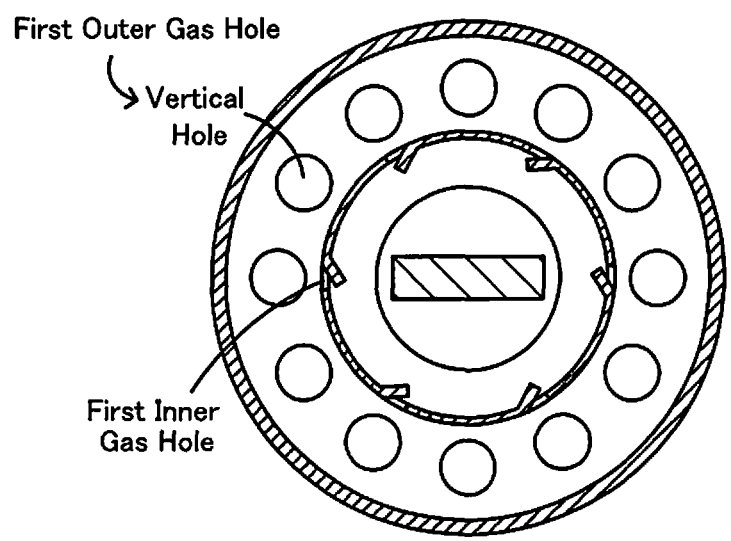
FIG. 21 is a cross-sectional view illustrating the arrangement of the first inner gas holes and the first outer gas holes of Experimental Example 13.

The following gas sensor is configured as Experimental Example 12. That is, all the 12 first outer gas holes are horizontal holes. The other values are the same as those of Experimental Example 2. In addition, the following gas sensor is configured as Experimental Example 13. That is, all the 12 first outer gas holes are the vertical holes. The other values are the same as those of Experimental Example 2. FIGS. 20 and 21 are cross-sectional views illustrating the arrangement of the first inner gas holes and the first outer gas holes of Experimental Examples 12 and 13, respectively. Table 2 shows the first-outer-hole count Nout, the number of horizontal holes, and the number of vertical holes of Experimental Examples 2, 12, and 13. Note that in Experimental Examples 12 and 13, the first inner gas holes are formed at equal intervals, and the first outer gas holes are formed at equal intervals.

[Evaluation Test 2]

A test that is the same as the evaluation test 1 was conducted to evaluate the gas sensors of Experimental Examples 2, 12, and 13 in terms of the heat-retaining effect and the responsiveness of gas concentration detection of the sensor element. Note that the flow velocity V of the measured gas was set to 30 m/s. The results of the evaluation are shown in Table 2 and FIG. 22.

TABLE 2

| | Hole Count | | | Test of Heat-Retaining Effect and Responsiveness Flow Velocity of V = 30 m/s | | | |
|---|---|---|---|---|---|---|---|
| | First- | | | Heat-Retaining Effect | | Responsiveness | |
| Experimental Examples | Outer- Hole Count Nout | Number of Horizontal Hole | Number of Vertical Hole | Mass Flow Rate Fin(kg/s) | Evaluation | Response Time (sec) | Evaluation |
| 2 | 12 | 6 | 6 | 2.85E−05 | ○ | 0.16 | ⊚ |
| 12 | 12 | 12 | 0 | 2.55E−05 | ○ | 0.20 | ⊚ |
| 13 | 12 | 0 | 12 | 2.68E−05 | ○ | 0.20 | ⊚ |

Figure 22:
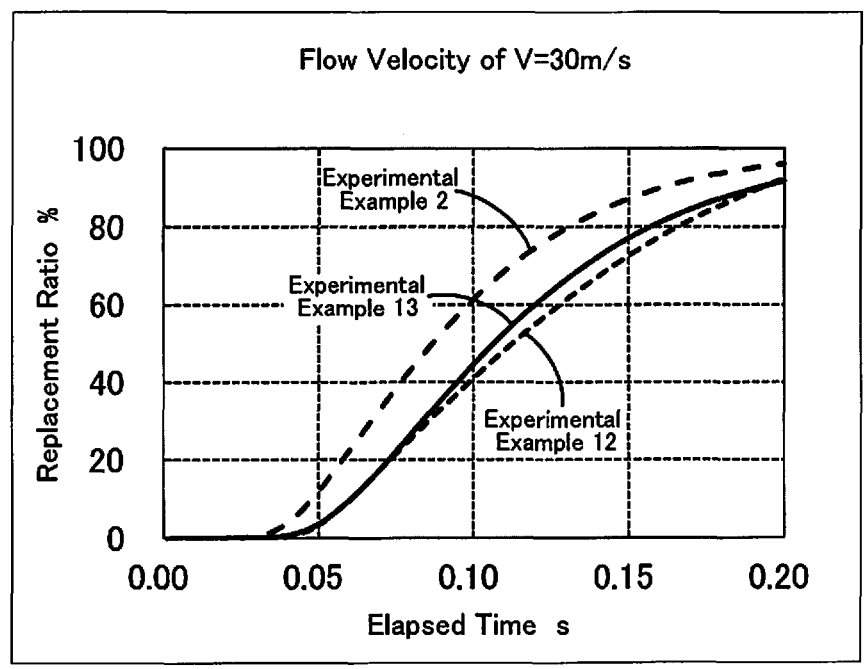
FIG. 22 is a graph representing a variation of a gas replacement ratio with time in a flow velocity V=30 m/s according Experimental Examples 2, 12 and 13.

As can be seen from Table 2 and FIG. 22, Experimental Example 2 having the first outer gas holes formed from the vertical holes and the horizontal hole alternately disposed has a shorter response time than Experimental Examples 12 and 13 having only vertical holes or only horizontal holes.

In addition, in Experimental Example 12 and Experimental Example 13, the response times are the same. Note that the value of the mass flow rate Fin of Experimental Example 2 is slightly higher than that of Experimental Examples 12 and 13. However, such a slight difference is negligible and, thus, the heat-retaining effects of Experimental Examples 2, 12, and 13 are substantially the same.

Experimental Examples 14 to 18

The following gas sensor is configured as Experimental Example 14. That is, the direction of the protection cover attached to the pipe 20 is biased by 30°. The other values are the same as those of Experimental Example 3. The following gas sensor is configured as Experimental Example 15. That is, the first-inner-hole count Nin=2, the inner/outer hole count ratio Nr=0.17, and the first-inner-hole non-existence maximum angle θinmax=175°. The other values are the same as those of Experimental Example 3. The following gas sensor is configured as Experimental Example 16. That is, the direction of the protection cover attached to the pipe 20 is biased by 30°. The other values are the same as those of Experimental Example 15. The following gas sensor is configured as Experimental Example 17. That is, the first-inner-hole count Nin=1, the inner/outer hole count ratio Nr=0.08, and the first-inner-hole non-existence maximum angle θinmax=355°. The other values are the same as those of Experimental Example 3. The following gas sensor is configured as Experimental Example 18. That is, the direction of the protection cover attached to the pipe 20 is biased by 30°. The other values are the same as those of Experimental Example 17. The first-outer-hole count Nout, the first-inner-hole count Nin, the inner/outer hole count ratio Nr, the first-outer-hole average area Aout, the first-inner-hole average area Ain, the inner/outer hole-area ratio Ar, the horizontal hole non-existence maximum angle θhmax, the vertical hole non-existence maximum angle θvmax, the first-outer-hole non-existence maximum angle θoutmax, the first-inner-hole non-existence maximum angle θinmax, and the distance L1 of each of the gas sensors of Experimental Example 3 and Experimental Examples 14 to 18 are shown in Table 3.

[Evaluation Test 3]

The gas sensors of Experimental Example 3 and Experimental examples 14 to 18 were evaluated in terms of the heat-retaining effect and the responsiveness of gas concentration detection of the sensor element. The evaluation was conducted as in Evaluation Test 1. The flow velocity V of the gas is set to 30 m/s. The relationship between the direction of the flow of the measured gas and each of the positions of the first outer gas hole and the first inner gas hole in each of Experimental Example 3 and Experimental Examples 14 to 18 is illustrated in FIGS. 23 to 28. In addition, the result of the evaluation test 3 is shown in Table 3 and FIG. 29.

TABLE 3

| Experimental Examples | Hole Count | | | Area | | | Horizontal Hole Non-Existence Maximum Angle θ hmax (°) | Vertical Hole Non-Existence Maximum Angle θ vmax (°) | First-Outer-Hole Non-Existence Maximum Angle θ outmax (°) |
|---|---|---|---|---|---|---|---|---|---|
| | First-Outer-Hole Count Nout | First-Inner-Hole Count Nin | Inner/Outer Hole Count Ratio Nr | First-Outer-Hole Average Area Aout (mm$^2$) | First-Inner-Hole Average Area Ain (mm$^2$) | Inner/Outer Hole-Area Ratio Ar | | | |
| 3 | 12 | 3 | 0.25 | 0.785 | 0.200 | 0.25 | 49 | 47 | 19 |
| 14 | 12 | 3 | 0.25 | 0.785 | 0.200 | 0.25 | 49 | 47 | 19 |
| 15 | 12 | 2 | 0.17 | 0.785 | 0.200 | 0.25 | 49 | 47 | 19 |
| 16 | 12 | 2 | 0.17 | 0.785 | 0.200 | 0.25 | 49 | 47 | 19 |
| 17 | 12 | 1 | 0.08 | 0.785 | 0.200 | 0.25 | 49 | 47 | 19 |
| 18 | 12 | 1 | 0.08 | 0.785 | 0.200 | 0.25 | 49 | 47 | 19 |

Figure 23:
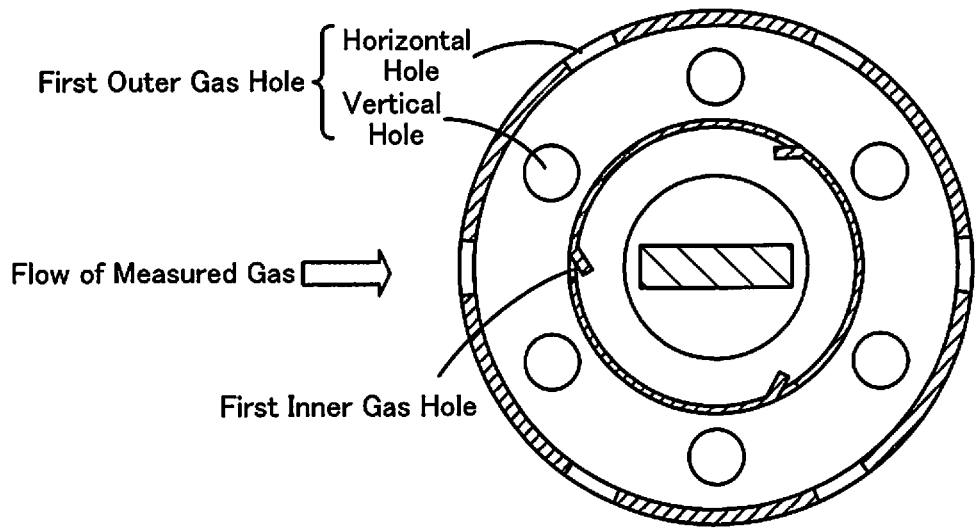
FIG. 23 is a cross-sectional view illustrating the positional relationship between the direction of the flow of the measured gas, the first outer gas holes and the first inner gas holes of Experimental Example 3.
Figure 24:
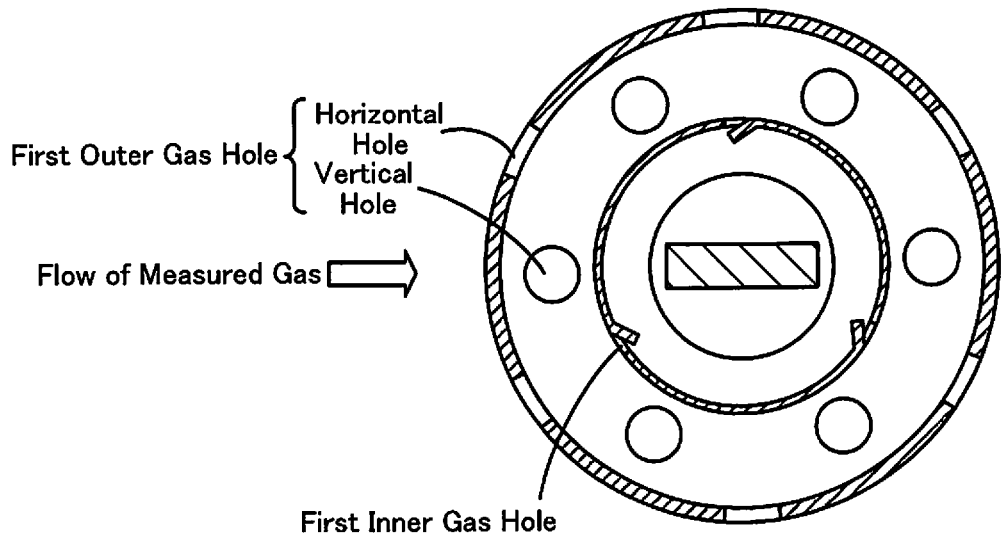
FIG. 24 is a cross-sectional view illustrating the positional relationship between the direction of the flow of the measured gas, the first outer gas holes and the first inner gas holes of Experimental Example 14.
Figure 25:
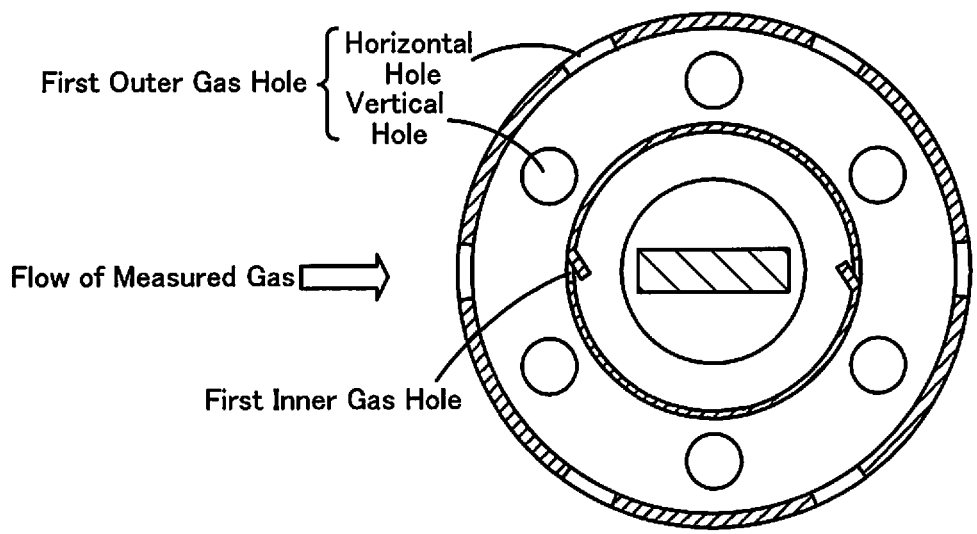
FIG. 25 is a cross-sectional view illustrating the positional relationship between the direction of the flow of the measured gas, the first outer gas holes and the first inner gas holes of Experimental Example 15.
Figure 26:
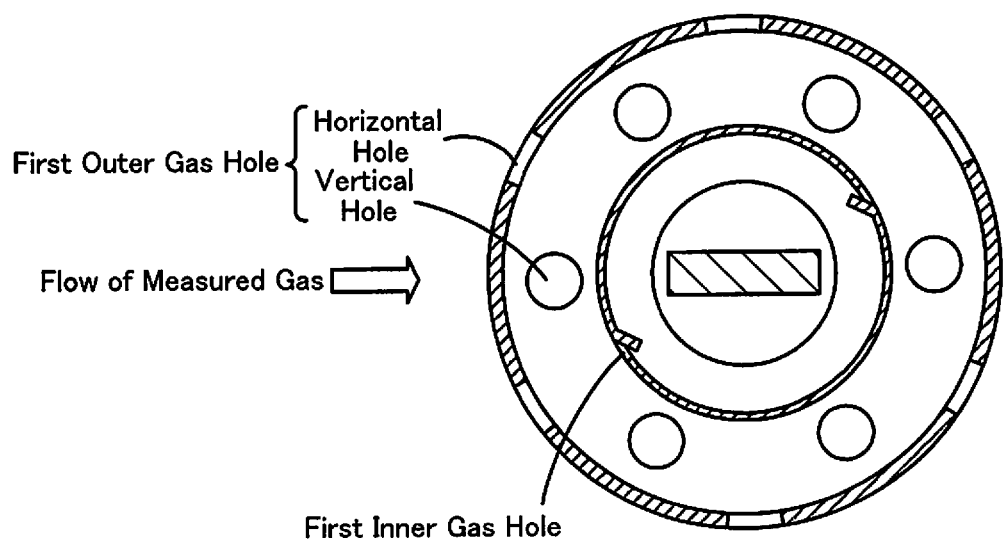
FIG. 26 is a cross-sectional view illustrating the positional relationship between the direction of the flow of the measured gas, the first outer gas holes and the first inner gas holes of Experimental Example 16.
Figure 27:
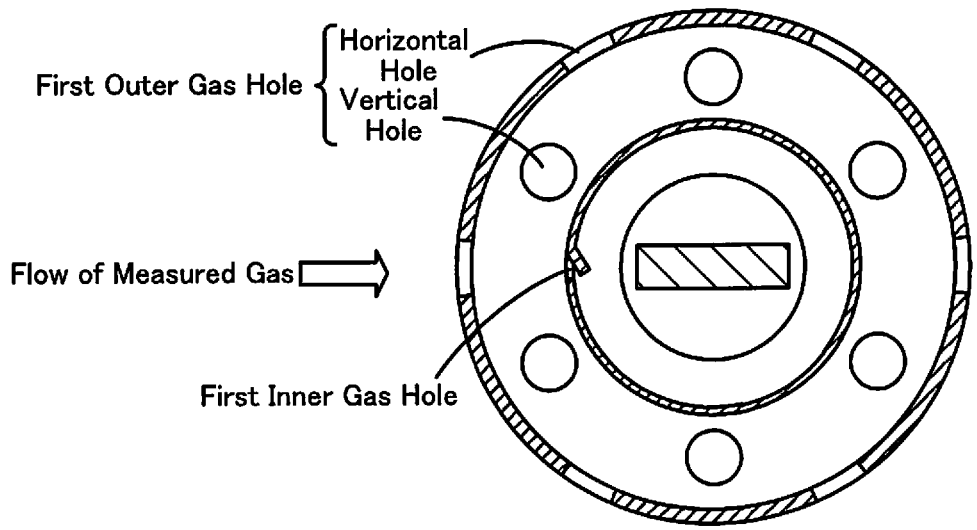
FIG. 27 is a cross-sectional view illustrating the positional relationship between the direction of the flow of the measured gas, the first outer gas holes and the first inner gas holes of Experimental Example 17.
Figure 28:
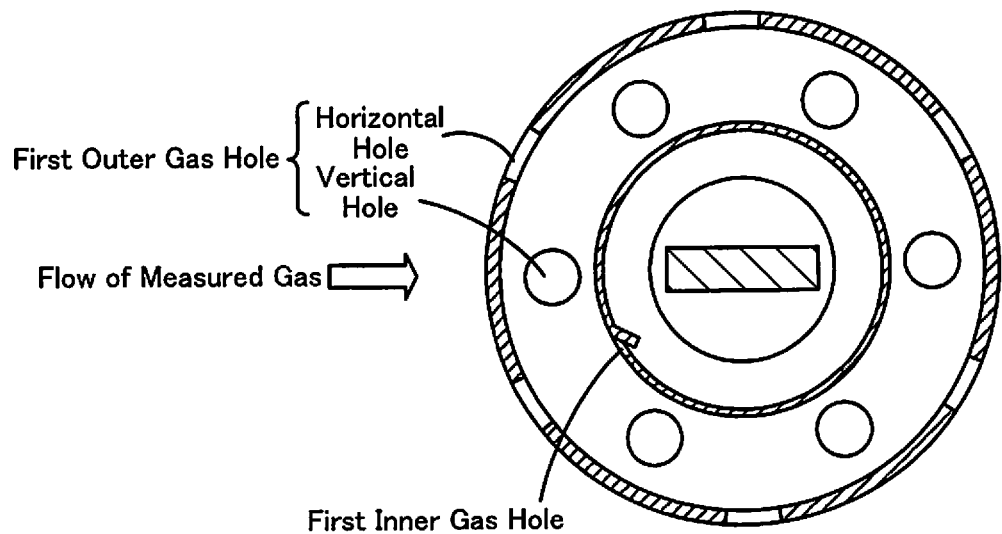
FIG. 28 is a cross-sectional view illustrating the positional relationship between the direction of the flow of the measured gas, the first outer gas holes and the first inner gas holes of Experimental Example 18.

| Experimental Examples | First-Inner-Hole Non-Existence Maximum Angle θ inmax (°) | Distance L1 (mm) | Positional Relationship between Measured Gas and Hole | Test of Heat-Retaining Effect and Responsiveness (Flow Velocity of V = 30 m/s) | | | |
|---|---|---|---|---|---|---|---|
| | | | | Heat-Retaining Effect | | Responsiveness | |
| | | | | Mass Flow Rate Fin(kg/s) | Evaluation | Response Time (sec) | Evaluation |
| 3 | 115 | 6.0 | FIG. 23 | 1.68E−05 | ⊚ | 0.25 | ○ |
| 14 | 115 | 6.0 | FIG. 24 | 1.69E−05 | ⊚ | 0.25 | ○ |
| 15 | 175 | 6.0 | FIG. 25 | 1.25E−05 | ⊚ | 0.32 | X |
| 16 | 175 | 6.0 | FIG. 26 | 1.30E−05 | ⊚ | 0.31 | X |
| 17 | 355 | 6.0 | FIG. 27 | 1.01E−05 | ⊚ | 0.53 | X |
| 18 | 355 | 6.0 | FIG. 28 | 9.70E−06 | ⊚ | 0.62 | X |

Figure 29:
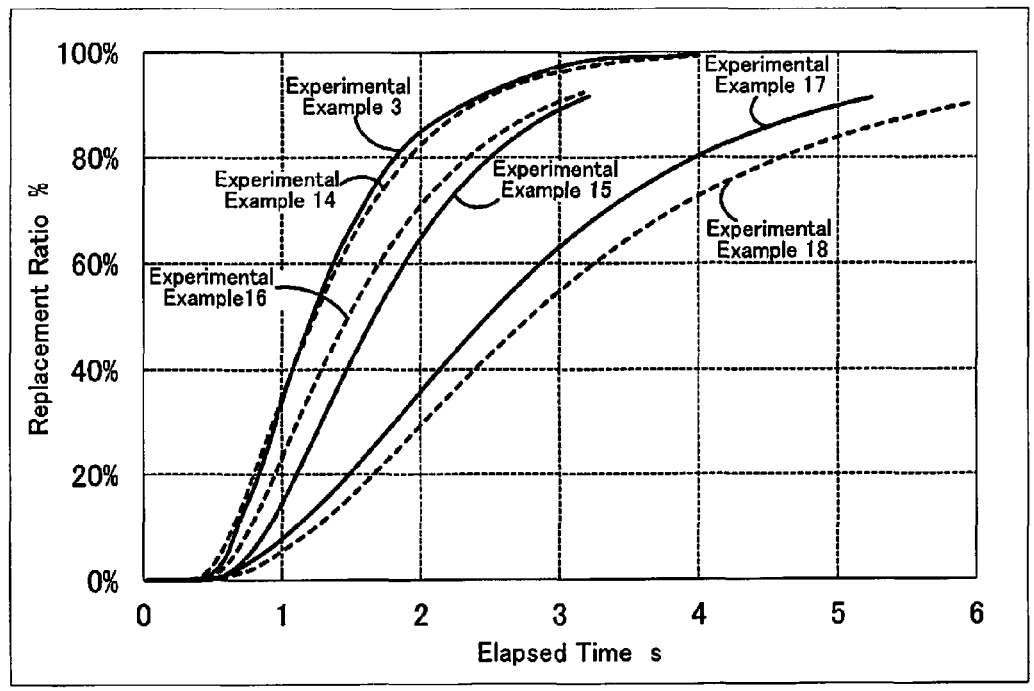
FIG. 29 is a graph representing a variation of a gas replacement ratio with time in a flow velocity V=30 m/s according Experimental Examples 3, 14 to 18.

As can be seen from Table 3 and FIG. 29, comparison of the response times of the two experimental examples in which only the directions of the flow of the measured gas differ from each other indicates that the difference in response time between Experimental Example 3 and Experimental Example 14 is the smallest, the difference in response time between Experimental Example 14 and Experimental Example 15 is the second smallest, and the difference in response time between Experimental Example 15 and Experimental Example 16 is the largest. This result suggests that a variation of the response time is smaller (i.e., a variation of the flow rate of the gas is smaller) with increasing first-inner-hole count Nin and, thus, decreasing first-inner-hole non-existence maximum angle θinmax even when the positional relationship between the direction of the flow of the measured gas and a direction t of the protection cover changes.

Experimental Example 19

Figure 30:
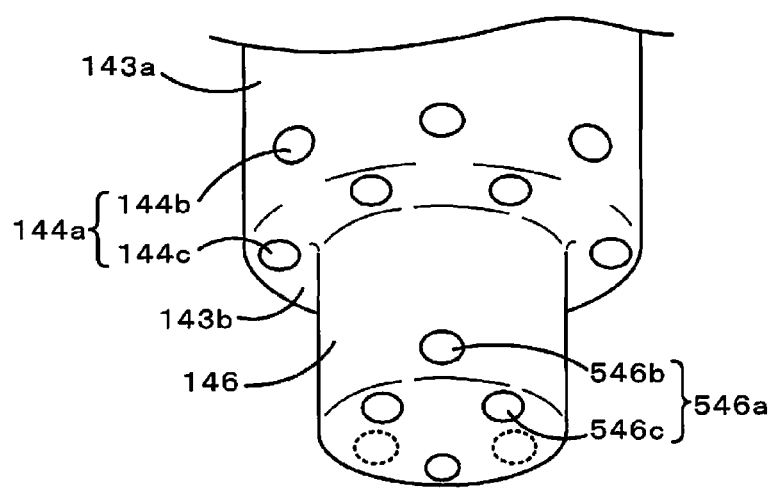
FIG. 30 is a view of the gas sensor of Experimental Example 19 viewed from the point of view the same as that of FIG. 4.
Figure 31:
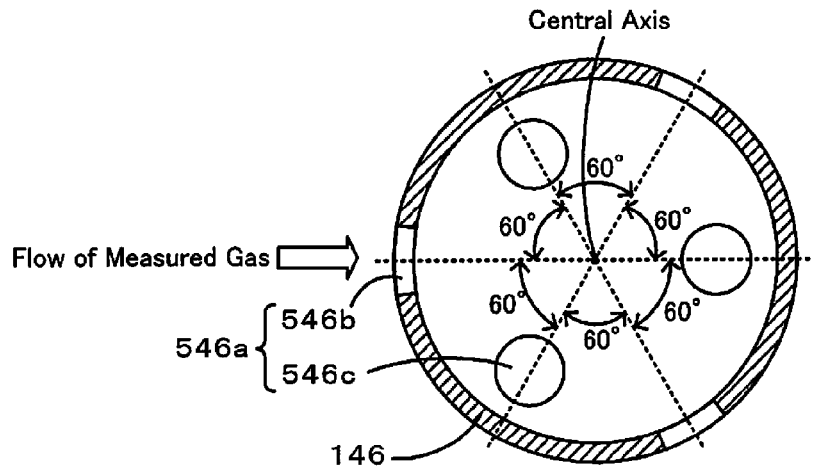
FIG. 31 is a cross-sectional view of the tip end portion 146 of the gas sensor of Experimental Example 19.

Experimental examples 19 to 21 are configured by changing the positions in the outer protection cover of the gas sensor of Experimental Example 2 at which the second outer gas holes 146a are formed in various ways. More specifically, as illustrated in FIGS. 30 and 31, the gas sensor of Experimental Example 19 is configured by forming six second outer gas holes 546a (three horizontal holes 546b formed in the side surface of the tip end portion 146 and three vertical holes 546c formed in the bottom surface of the tip end portion 146) instead of the second outer gas holes 146a of Experimental Example 2. Note that FIG. 30 is a view of the gas sensor of Experimental Example 19 viewed from the point of view the same as that of FIG. 4 (corresponding to the view on Arrow D of FIG. 2). FIG. 31 is a cross-sectional view of the tip end portion 146 of the gas sensor of Experimental Example 19. FIG. 31 is a view of the bottom surface of the tip end portion 146 viewed from the cross section that is perpendicular to the central axis of the gas sensor and that passes through the central point of the horizontal hole 546b. Note that the horizontal holes 546b are formed at equal intervals. That is, the neighboring straight lines between the central point of one of the horizontal hole 546b and the central axis of the gas sensor form an angle of 120°. Similarly, the vertical holes 546c are formed at equal intervals. In addition, the horizontal holes 546b and the vertical hole 546c are formed so as to be staggered relative to each other in the cross section of FIG. 31 (the angle formed by the line extending between the central point of one of the horizontal holes 546b and the central axis of the gas sensor and the line extending between the central point of the neighboring vertical hole 546c and the central axis of the gas sensor is 60°). Each of the horizontal hole 546b and the vertical hole 546c is a circular hole (the exact circle) whose inner diameter is 1.2 mm, which is the same as the inner diameter of the second outer gas hole 146a.

Experimental Example 20

Figure 32:
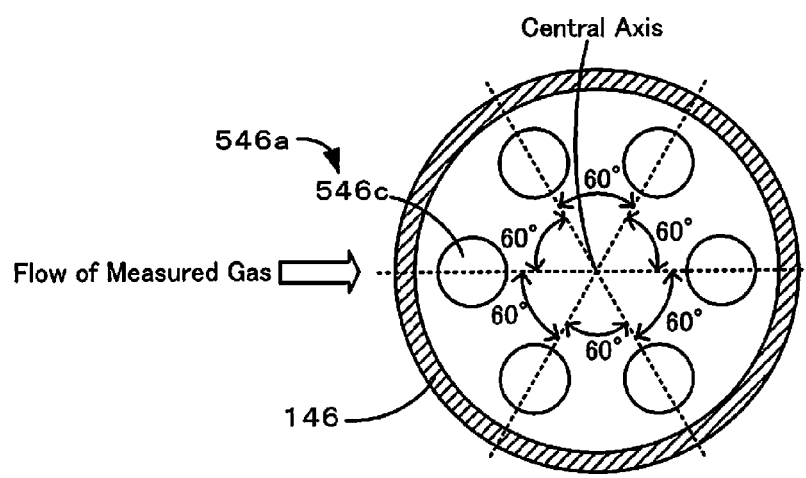
FIG. 32 is a cross-sectional view of the tip end portion 146 of a gas sensor of Experimental Example 20.

The following gas sensor is configured as Experimental Example 20. That is, the second outer gas holes 546a do not include the horizontal hole 546b. Instead, the second outer gas holes 546a include six vertical holes 546c. The other values are the same as those of Experimental Example 19. FIG. 32 is a cross-sectional view of the tip end portion 146 of a gas sensor of Experimental Example 20. FIG. 32 is a cross-sectional view that is the same as FIG. 31. The vertical hole 546c are formed at equal intervals. That is, the angle formed by a line extending between the central point of one of the vertical holes 546c and the central axis of the gas sensor and a line extending between the central point of a neighboring horizontal hole 546c and the central axis of the gas sensor is 60°.

Experimental Example 21

Figure 33:
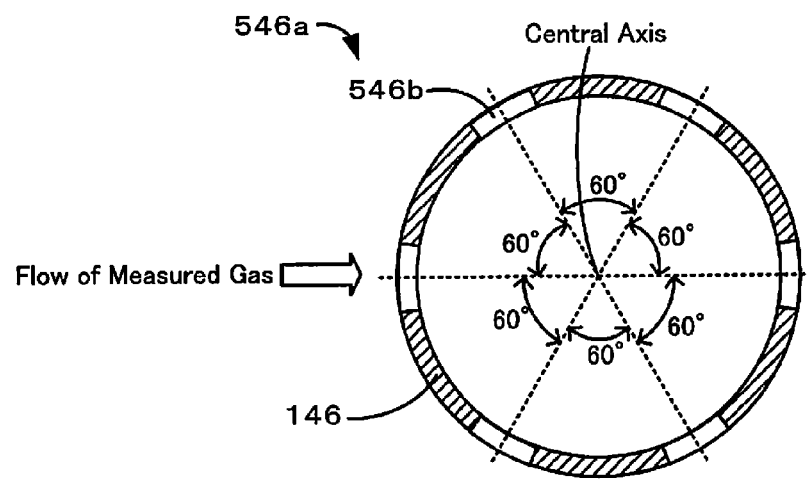
FIG. 33 is a cross-sectional view of the tip end portion 146 of a gas sensor of Experimental Example 21.

The following gas sensor is configured as Experimental Example 21. That is, the second outer gas holes 546a do not include the vertical hole 546c. Instead, the second outer gas holes 546a include six horizontal hole 546b. The other values are the same as those of Experimental Example 19. FIG. 33 is a cross-sectional view of the tip end portion 146 of a gas sensor of Experimental Example 21. FIG. 33 is a cross-sectional view that is the same as FIG. 31. The horizontal hole 546b are formed at equal intervals. That is, the angle formed by a line extending between the central point of one of the horizontal holes 546b and the central axis of the gas sensor and a line extending between the central point of a neighboring vertical hole 546b and the central axis of the gas sensor is 60°.

[Evaluation Test 4]

Like Evaluation Test 1, the gas sensors of experimental examples 19 to 21 were evaluated in terms of the heat-retaining effect and the responsiveness of gas concentration detection of the sensor element. Note that in FIGS. 31 to 33, the direction of the flow of the measured gas in Evaluation Test 4 is also illustrated.

[Evaluation Test 5]

Figure 34:
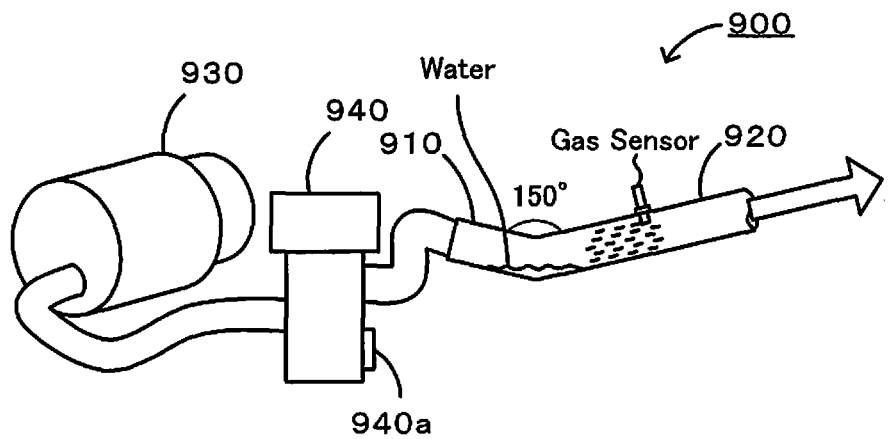
FIG. 34 illustrates a water amount measuring device 900.

The gas sensors of Experimental Example 2 and Experimental Examples 19 to 21 were examined in terms of the amount of water wetting the tip end of the sensor element. The amount of water was measured by using a water amount measuring device 900 illustrated in FIG. 34. That is, the water amount measuring device 900 was formed by connecting two pipes 910 and 920 each having a diameter of 28 mm with each other so as to form an angle of 150°, connecting an air blower 930 at a point 300 mm away from the connection point via a selector valve 940, and disposing the gas sensor 400 mm away from the connection point, on the opposite side from the air blower 930. Thereafter, the air blower 930 was operated under predetermined drive conditions with the connection portion filled with 100-ml water to send wind into the pipe. By sending the wind, the water stored in the connection portion was sprayed toward the gas sensor, and all the stored water was discharged to the outside of the pipe 920. During the period of time, the power of the internal heater was controlled so that the temperature of the sensor element 110 was maintained at a target value of 100° C. If water is deposited on the tip end of the sensor element 110, the power control value of the heater increases since the temperature decreases. Accordingly, as the power control value increases, the amount of water wetting the sensor element 110 increases (the water wetting resistance decreases). Note that the predetermined drive conditions of the air blower 930 are that after the heater of the sensor element 110 is stably maintained at a temperature of 100° C., the air is moved at about 50 m/s with the selector valve 940 connected to a bypass 940a, the selector valve 940 is switched to the pipe 910, and the air is delivered to the pipe 910 for 3 seconds. Note that in Evaluation Test 5, it is evaluated that the water wetting resistance properties are fair (a circle) if the power control value is 0.05 or lower.

The number and the arrangement of first outer gas holes, the number and the arrangement of second outer gas holes, and the results of Evaluation Test 4 and Evaluation Test 5 for the gas sensors of Experimental Example 2 and Experimental Examples 19 to 21 are shown in Table 4.

TABLE 4

| | First Outer Gas Hole | | | Second Outer Gas Hole | | | | Test of Heat-Retaining Effect and Responsiveness Flow Velocity of V = 30 m/s | | | | Water Wetting Test Water Wetting Resistance Property | |
|---|---|---|---|---|---|---|---|---|---|---|---|---|---|
| | | | | | | | | Heat-Retaining Effect | | Responsiveness | | Power | |
| Experimental Examples | First-Outer-Hole Count Nout | Number of Horizontal Hole | Number of Vertical Hole | Second-Outer-Hole Count | Number of Horizontal Hole | Number of Vertical Hole | Number of Hole formed in Corner Portion | Mass Flow Rate Fin(kg/s) | Evaluation | Response Time (sec) | Evaluation | Control Value of Heater | Evaluation |
| 2 | 12 | 6 | 6 | 6 | 0 | 0 | 6 | 2.85E−05 | ○ | 0.16 | ◎ | 0.03 | ○ |
| 19 | 12 | 6 | 6 | 6 | 3 | 3 | 0 | 2.70E−05 | ○ | 0.18 | ◎ | 0.02 | ○ |
| 20 | 12 | 6 | 6 | 6 | 0 | 6 | 0 | 2.90E−05 | ○ | 0.11 | ◎ | 0.08 | X |
| 21 | 12 | 6 | 6 | 6 | 6 | 0 | 0 | 1.50E−05 | ◎ | 0.30 | ○ | 0.01 | ○ |

[Relationship Between Mass Flow Rate Fin and Cooling Level of Sensor Element]

Figure 35:
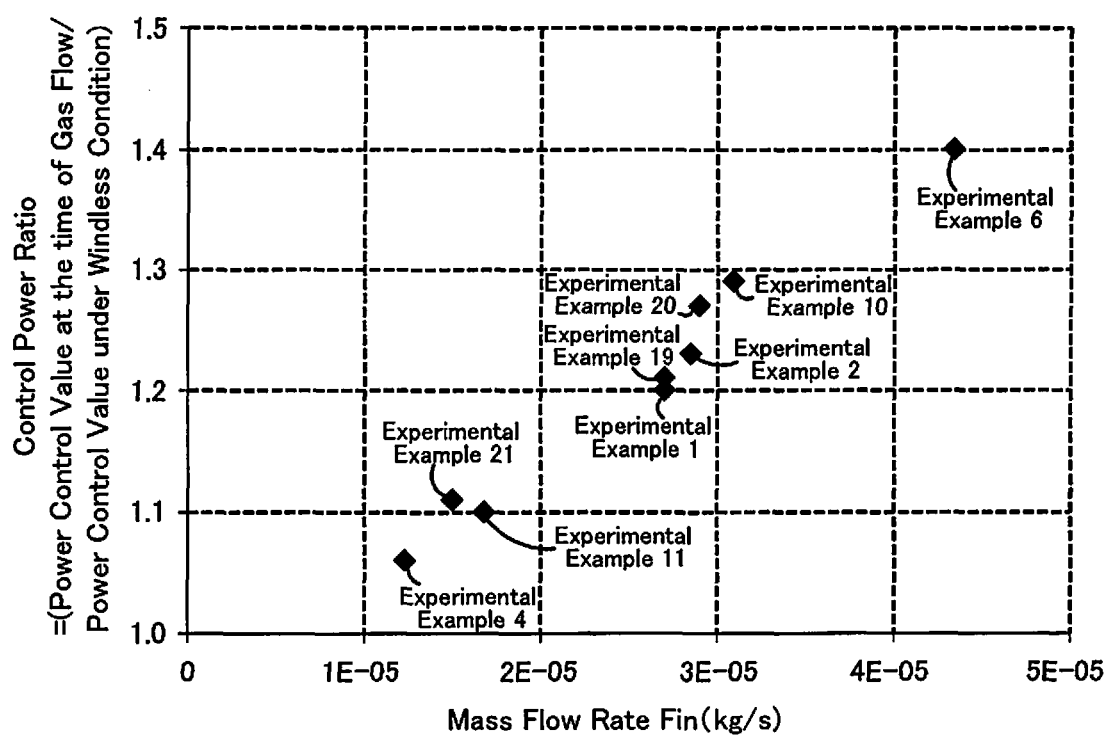
FIG. 35 is a graph representing a relationship between the value of a mass flow rate Fin and a control power ratio.

A relationship between the mass flow rate Fin and the cooling level of the sensor element of Experimental Examples 1, 2, 4, 6, 10, 11 and Experimental Examples 19 to 21 were examined. More specifically, as in Evaluation Tests 1 and 4, for each of the gas sensors of Experimental Examples, the gas sensor was attached to the pipe filled with air. The inside of the pipe was kept under windless conditions. Then, the internal heater was controlled so that the sensor element 110 was maintained at a target temperature of 850° C. After the power control value of the heater became stable, the power control value was measured. The measured value was defined as the power control value under windless conditions. Thereafter, as in Experimental Examples 1 and 4, the measured gas was moved through the pipe at a predetermined flow velocity of V (=30 m/s). During the period of time, the power of the internal heater was controlled so that the sensor element 110 was maintained at a target temperature of 850° C. The difference between the power control value obtained under windless conditions and the power control value obtained when the measured gas is delivered (="stable power control value−the above-described 'power control value under windless conditions'") was measured. The difference was defined as the power control value at the time of gas flow. Thereafter, a control power ratio=(the power control value at the time of gas flow/the power control value under windless conditions) is calculated. A relationship between the values of the mass flow rates Fin (the same value as in Evaluation Tests 1 and 4) and the control power ratio of each of the Experimental Examples 1, 2, 4, 6, 10, and 11 and Experimental Examples 19 to 21 are shown in Table 5 and FIG. 35. As can be seen from Table 5 and FIG. 35, the control power ratio increases with increasing mass flow rate Fin. At that time, the control power ratio increases as the temperature of the sensor element 110 decreases due to the flow of the measured gas. Accordingly, Table 5 and FIG. 35 indicate that the gas sensor having a smaller mass flow rate Fin has a smaller control power ratio, that is, a higher heat-retaining effect of the sensor element.

TABLE 5

| Experimental Examples | Mass Flow Rate Fin(kg/s) | Control Power Ratio |
|---|---|---|
| 1 | 2.70E−05 | 1.20 |
| 2 | 2.85E−05 | 1.23 |
| 4 | 1.23E−05 | 1.06 |
| 6 | 4.34E−05 | 1.40 |
| 10 | 3.09E−05 | 1.29 |
| 11 | 1.68E−05 | 1.10 |
| 19 | 2.70E−05 | 1.21 |
| 20 | 2.90E−05 | 1.27 |
| 21 | 1.50E−05 | 1.11 |

Note that Experimental Examples 1 to 3 and Experimental Examples 11 to 14 correspond to the embodiment of the present invention, and Experimental Examples 4 to 10 and Experimental Examples 15 to 18 correspond to comparative examples. In addition, Experimental Examples 19 to 21 correspond to the embodiment of the present invention.

The present application claims priority from Japanese Patent Application No. 2013-068868 filed on Mar. 28, 2013, the entire contents of which are incorporated herein by reference.

INDUSTRIAL APPLICABILITY

The present invention is applicable to a gas sensor that detects the concentration of predetermined gas, such as NOx or oxygen, in measured gas, such as exhaust gas of a motor vehicle.

REFERENCE SIGNS LIST 20 pipe, 22 fixing member, 100 gas sensor, 102 housing, 103 nut, 110 sensor element, 120 protection cover, 122 first gas chamber, 124 sensor element chamber, 126 second gas chamber, 130 inner protection cover, 132 large-diameter portion, 133 stepped portion, 134 first body portion, 134a first inner gas hole, 134b guide portion, 135 stepped portion, 136 second body portion, 137 stepped portion, 138 end portion, 138a second inner gas hole, 140 outer protection cover, 142 large-diameter portion, 143 body portion, 143a side portion, 143b stepped portion, 144a first outer gas hole, 144b horizontal hole, 144c vertical hole, 146 tip end portion, 146a second outer gas hole, 146b corner portion, 146c area, 200 gas sensor, 224 sensor element chamber, 230 inner protection cover, 234a first inner gas hole, 234b guide portion, 236 body portion, 300 gas sensor, 330 inner protection cover, 338 tip end portion, 338a second inner gas hole, 400 gas sensor, 430 inner protection cover, 434a first inner gas hole, 434b guide portion, 436 body portion, 438 tip end portion, 438*a* second inner gas hole, 446*a* second outer gas hole, 546*a* second outer gas hole, 546*c* vertical hole, 900 water amount measuring device, 910, 920 pipe, 930 air blower, 940 selector valve, 940*a* bypass.

What is claimed is:

1. A gas sensor including:
a sensor element capable of detecting the concentration of predetermined gas in measured gas,
an inner protection cover having a bottomed cylindrical shape and covering a tip end of the sensor element, where the inner protection cover has at least three first inner gas holes and at least one second inner gas hole formed at a position further away in a tip direction of the sensor element than the at least three first inner gas holes,
an outer protection cover having a bottomed cylindrical shape and covering the inner protection cover, where the outer protection cover includes a cylindrical body portion having a plurality of first outer gas holes formed therein and a bottomed cylindrical tip end portion having at least one second outer gas hole formed therein and having an inner diameter that is smaller than an inner diameter of the body portion,
a first gas chamber formed as a space between the body portion of the outer protection cover and the inner protection cover, where the first gas chamber communicates with the inside of the inner protection cover through the at least three first inner gas holes, and
a second gas chamber formed as a space between the tip end portion of the outer protection cover and the inner protection cover, where the second gas chamber does not directly communicate with the first gas chamber and communicates with the inside of the inner protection cover through the at least one second inner gas hole,
wherein the at least three first inner gas holes and the plurality of first outer gas holes are formed so that the following conditions are satisfied: 0<an inner/outer hole count ratio Nr≤0.5 and 0<an inner/outer hole-area ratio Ar≤0.25, and
wherein a first-inner-hole count Nin represents a total number of the at least three first inner gas holes, a first-inner-hole average area Ain [mm$^2$] represents (a total opening area of the at least three first inner gas holes)/(the first-inner-hole count Nin), a first-outer-hole count Nout represents a total number of the plurality of first outer gas holes, a first-outer-hole average area Aout [mm$^2$] represents (a total opening area of the plurality of first outer gas holes)/(the first-outer-hole count Nout), the inner/outer hole count ratio Nr represents the first-inner-hole count Nin/the first-outer-hole count Nout, and the inner/outer hole-area ratio Ar represents (the first-inner-hole average area Ain/the first-outer-hole average area Aout).

2. The gas sensor according to claim 1,
wherein the body portion of the outer protection cover includes a side portion having a side surface extending in the direction of the central axis of the outer protection cover and a stepped portion that connects the side portion to the tip end portion,
the plurality of first outer gas holes includes at least three horizontal holes formed in the side portion of the outer protection cover and at least three vertical holes formed in the stepped portion of the outer protection cover,
the horizontal holes are formed such that 0≤a horizontal hole non-existence maximum angle θhmax≤180°, wherein when the horizontal holes and the central axis of the outer protection cover are projected onto a plane that is perpendicular to the central axis to form a projected central axis and projected horizontal holes and the plane is viewed from the projected central axis in a radial direction of the outer protection cover, an area of the plane in which the projected horizontal holes do not exist is referred to as a horizontal hole non-existence area, and a largest angle among central angles of the horizontal hole non-existence area is referred to as the horizontal hole non-existence maximum angle θhmax, and;
the vertical holes are formed so that 0 a vertical hole non-existence maximum angle θvmax≤180°, wherein when the vertical holes and the central axis of the outer protection cover are projected onto a plane that is perpendicular to the central axis to form a second projected central axis and projected vertical holes and the plane is viewed from the second projected central axis in a radial direction of the outer protection cover, an area of the plane in which the projected vertical holes do not exist is referred to as a vertical hole non-existence area, and a largest angle among central angles of the vertical hole non-existence areas is referred to as the vertical hole non-existence maximum angle θvmax.

3. The gas sensor according to claim 2,
wherein the horizontal holes and the vertical holes are formed so as to be alternately disposed in a circumferential direction of the outer protection cover when the horizontal holes and the vertical holes are projected onto the plane that is perpendicular to the central axis of the outer protection cover.

4. The gas sensor according to claim 1,
wherein the at least three first inner gas holes are formed such that the first-inner-hole count Nin≥3 and 0≤a first-inner-hole non-existence maximum angle θinmax≤180°, wherein when the at least three first inner gas holes and the central axis of the inner protection cover are projected onto a plane that is perpendicular to the central axis to form a third projected central axis and projected first inner gas holes and the plane is viewed from the third projected central axis in a radial direction of the inner protection cover, an area of the plane in which the projected first inner gas holes do not exist is referred to as a first-inner-hole non-existence area, and a largest angle among central angles of the first-inner-hole non-existence area is referred to as the first-inner-hole non-existence maximum angle θinmax, and
the plurality of first outer gas holes is formed such that the first-outer-hole count Nout≥6 and 0≤a first-outer-hole non-existence maximum angle θoutmax≤90°, wherein when the plurality of first outer gas holes and the central axis of the outer protection cover are projected onto a plane that is perpendicular to the central axis to form a fourth projected central axis and projected first outer gas holes and the plane is viewed from the fourth projected central axis in a radial direction of the outer protection cover, an area of the plane in which the projected first outer gas holes do not exist is referred to as a first-outer-hole non-existence area, and a largest angle among central angles of the first-outer-hole non-existence area is referred to as the first-outer-hole non-existence maximum angle θoutmax.

5. The gas sensor according to claim 4,
wherein the at least three first inner gas holes are formed such that the first-inner-hole count $N_{in} \geq 3$ and $0 \leq$ the first-inner-hole non-existence maximum angle $\theta_{inmax} \leq 120°$, and
the plurality of first outer gas holes is formed such that the first-outer-hole count $N_{out} \geq 6$ and $0 \leq$ the first-outer-hole non-existence maximum angle $\theta_{outmax} \leq 60°$.

6. The gas sensor according to claim 1,
wherein the plurality of first outer gas holes is formed such that an opening area of each of the first outer gas holes ranges from $0.196 \text{ mm}^2$ to $3.14 \text{ mm}^2$.

7. The gas sensor according to claim 1,
wherein each of the at least three first inner gas holes has an opening area of $0.2 \text{ mm}^2$ or greater.

8. The gas sensor according to claim 1,
wherein a central point of an opening of each of the at least three first inner gas holes is located 5 mm or more away from the tip end of the sensor element towards a rear end of the sensor element.

9. The gas sensor according to claim 1,
wherein the at least one second outer gas hole includes at least three horizontal holes formed in a side surface of the tip end portion and at least three vertical holes formed in a bottom surface of the tip end portion.

10. The gas sensor according to claim 1,
wherein the plurality of first outer gas holes is formed such that an opening area of each of the plurality of first outer gas holes ranges from $0.785 \text{ mm}^2$ to $3.14 \text{ mm}^2$.

* * * * *